(12) United States Patent
Erbacher et al.

(10) Patent No.: US 7,683,035 B1
(45) Date of Patent: *Mar. 23, 2010

(54) METHOD OF STABILIZING AND/OR ISOLATING NUCLEIC ACIDS

(75) Inventors: Christoph Erbacher, Haan (DE); Helge Bastian, Mettmann (DE); Ralf Wyrich, Dormagen (DE); Uwe Oelmüller, Erkrath (DE); Thomas Manz, Düsseldorf (DE)

(73) Assignee: Qiagen, GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/510,534

(22) Filed: Feb. 22, 2000

(30) Foreign Application Priority Data

Feb. 23, 1999 (EP) .................................. 99103457

(51) Int. Cl.
*A01N 43/04* (2006.01)
*A61K 31/70* (2006.01)
*G01N 1/00* (2006.01)
*A61K 9/127* (2006.01)
*C12Q 1/68* (2006.01)
*C12N 5/00* (2006.01)
*C12N 15/88* (2006.01)

(52) U.S. Cl. .................. 514/44; 436/176; 424/450; 435/6; 435/325; 435/458

(58) Field of Classification Search ............. 536/23.1, 536/25.4, 25.41; 435/6, 238; 514/42, 642
See application file for complete search history.

(56) References Cited

U.S. PATENT DOCUMENTS

| | | | |
|---|---|---|---|
| 3,770,720 A | | 11/1973 | Butti et al. |
| 3,899,481 A | | 8/1975 | Butti et al. |
| 4,843,155 A | | 6/1989 | Chomczynski |
| 5,010,183 A | * | 4/1991 | Macfarlane |
| 5,234,809 A | | 8/1993 | Boom et al. |
| 5,300,635 A | | 4/1994 | MacFarlane |
| 5,674,908 A | * | 10/1997 | Haces .................. 514/642 |
| 5,728,822 A | | 3/1998 | Macfarlane |
| 5,834,439 A | * | 11/1998 | Haces .................. 514/42 |
| 6,093,564 A | * | 7/2000 | Budowsky .................. 435/238 |
| 6,733,777 B2 | * | 5/2004 | Erbacher et al. .................. 424/450 |

FOREIGN PATENT DOCUMENTS

| | | |
|---|---|---|
| EP | 0 338 591 A2 | 10/1989 |
| EP | 0 442 026 B1 | 12/1995 |
| EP | 0 707 077 A2 | 4/1996 |
| EP | 0 726 312 A2 | 8/1996 |
| EP | 0 773 295 | 5/1997 |
| EP | 773295 A2 * | 5/1997 |
| SU | 1081171 | 3/1984 |
| WO | WO 94/18156 | 8/1994 |
| WO | WO 95/17373 | 6/1995 |
| WO | WO 97/42819 * | 11/1997 |
| WO | WO 98/19709 | 5/1998 |
| WO | WO 9819709 A2 * | 5/1998 |
| WO | WO 99/22021 | 5/1999 |

OTHER PUBLICATIONS

P. Sykora et al. Elmination of Plasmids pKM 101 and F'lac from *Salmonella typhimurium* and *Escherichia coli* by Bisammonium Salt. Folia Microbiol. vol. 36, No. 3, pp. 240-245 (1991).*
Chirgwin et al., *Biochem.* 18: 5294-5299 (1979).
Chomczynski and Sacchi, *Anal. Biochem.* 162: 156-159 (1987).
Horniak et al., *Chemical Abstracts* 3(110): 20127 (1989).
Horniak et al., *Stud. Biophys.* 124(1): 61-68 (1998).
Schmidt et al. *J. Med. Virol.* 47: 153-160 (1995).
Sykora et al., *Chemical Abstracts* 7(115): 66241 (1991).
Sykora et al., *Chemical Abstracts* 25(115): 275625 (1991).
Sykora et al., *Folia Microbiol* 36(3): 240-245 (1991).
Wallace, *Meth. Enzym.* 152: 33-41 (1987).
Fujii, *Analytica Chimica Acta*, 200: 181-189 (1987).
Gabbay, *Biopolymers*, 5: 727-747 (1967).
Gabbay et al., *Biopolymers*, 6: 255-268 (1968).
Glaser et al., *Biopolymers*, 6: 243-254 (1968).
Database WPI Section Ch, Week 8445 Derwent Publications Ltd., London, GB; An 84-281416 XP002111373 & SU 1 081 171 A (KIEV Dotors Train), Mar. 23, 1984.
Gabbay et al., *Biopolymers*, 6: 993-996 (1968).
Gabbay et al., *J.A.C.S.*, 89(26): 7123-7125 (1967).
*Total QuickRNA Handbook*, product manual, Talent srl. (Trieste, IT).

* cited by examiner

*Primary Examiner*—Janet L. Epps-Smith
(74) *Attorney, Agent, or Firm*—Yankwich & Associates, P.C.; Leon R. Yankwich; Michael R. Wesolowski

(57) ABSTRACT

The present invention relates to a method of stabilizing and/or isolating nucleic acids, wherein a biological sample containing nucleic acids is contacted with a cationic compound. The invention also relates to said cationic compound per se and to the use of said cationic compound in stabilizing and/or isolating nucleic acids. Furthermore, the invention relates to pharmaceutical compositions, diagnostic compositions, and to compositions used in research, which include cationic compounds or a complex being formed upon contact of said cationic compound with a nucleic acid.

34 Claims, 5 Drawing Sheets

Figure 1:
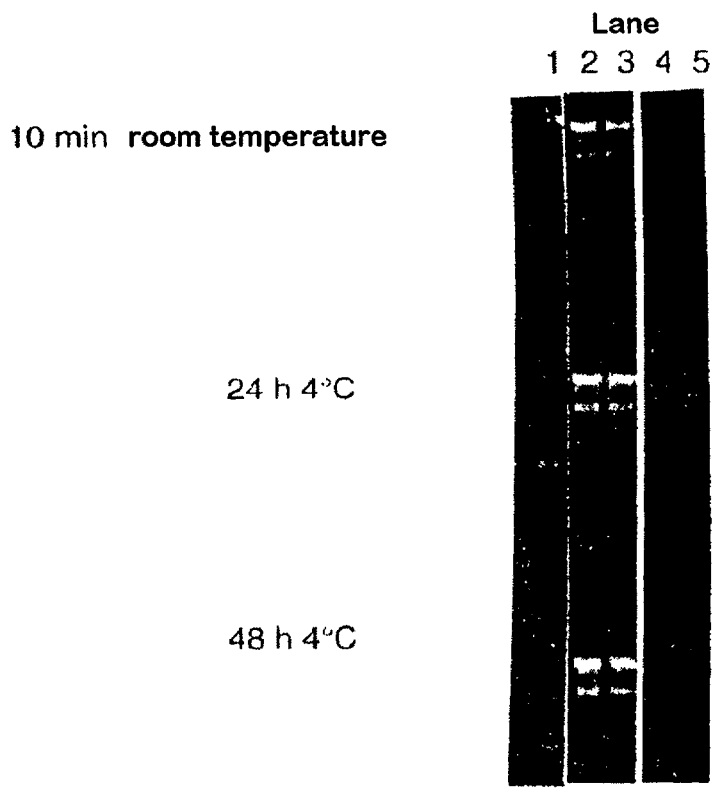

Figure 1: RNA Integrity

All samples are prepared in double determinations. 30 l of eluate at a time is separated on a 1.2% agarose/formaldehyde/MOPS gel.

Lane 1:     Length marker 0.24 - 9.5 kb
Lane 2/3:   HeLa RNA stabilized with ethanediyl-1,2-bis(dimethyldecylammonium bromide)
Lane 4/5:   Control

| Cationic substance: | A | B | D | E | K |
|---|---|---|---|---|---|
| Concentration % (w/v): | 2 | 2 | 5 | 2 | |

METHOD OF STABILIZING AND/OR ISOLATING NUCLEIC ACIDS

CROSS REFERENCE TO RELATED APPLICATIONS

This application is United States filing under 35 U.S.C. §111(a) and claims priority to European Patent Application No. 99 10 3457.0, filed Feb. 23, 1999.

Method of Stabilizing and/or Isolating Nucleic Acids The present invention relates to a method of stabilizing and/or isolating nucleic acids, wherein a biological sample containing nucleic acids is contacted with a cationic compound. The invention also relates to said cationic compound per se and to the use of said cationic compound in stabilizing and/or isolating nucleic acids. Furthermore, the invention relates to pharmaceutical compositions, diagnostic compositions, and to compositions used in research, which include cationic compounds or a complex being formed upon contact of said cationic compound with a nucleic acid.

It has been known for long that it is possible to determine and examine the genetic origin and functional activity of a cell by studying its nucleic acids. Analyses of nucleic acids enable direct access to the cause of cell activities. Thus, they are potentially superior to indirect, conventional methods such as detection of metabolic products. Consequently, a massive increase of nucleic acid analyses is to be expected in future. Thus, molecular-biological analyses are already used in various fields, e.g. in medical and clinical diagnostics, in pharmacy in the development and evaluation of drugs, in food analytics and in food production monitoring, in agriculture in breeding useful plants and livestock, as well as in environmental analytics and in numerous fields of research.

By analyzing the RNA, specifically the mRNA in cells, direct determination of the activities of genes is possible. The quantitative analysis of transcript patterns (mRNA patterns) in cells using modern molecular-biological methods such as real-time reverse transcriptase PCR (real-time RT PCR) or gene expression chip analyses permits e.g. the recognition of incorrectly expressed genes, thereby allowing the recognition of e.g. metabolic diseases, infections, or the development of cancer. By analyzing the DNA from cells using molecular-biological methods such as PCR, RFLP, AFLP or sequencing, it is possible e.g. to detect genetic defects or to determine the type of HLA and other genetic markers.

The analysis of genomic DNA and RNA is also used in the direct detection of infectious pathogens such as viruses, bacteria, etc.

One indispensable precondition for nucleic acid analytics is immediate stabilization of the nucleic acids after the biological sample has been extracted from its natural environment. This applies for DNA and RNA, particularly for RNA which may undergo exceedingly rapid degradation once the biological sample has been extracted. On the other hand, extraction of the biological sample may be followed by synthesis of new mRNA molecules as a result of e.g. induction of stress genes, so that the transcript pattern of the cells could be changed. In this way, subsequent analyses may be distorted.

To date, it is barely possible to stabilize nucleic acids, particularly over a prolonged period of time, e.g. for several hours or days and up to weeks when using means suitable for routine analyses. This is highly disadvantageous because, e.g. in the medical field, e.g. in a medical practice, it is often the case that samples containing nucleic acids are collected which can be put to further examination only after prolonged storage and transportation to a laboratory.

In the meantime, the nucleic acids contained in the samples may undergo changes or even complete decomposition. Obviously, this has a massive impact on the results of tests conducted at a later time, or renders them completely impossible. Molecular-biological techniques such as PCR, reverse transcription PCR (RT PCR), SunRise, LCR, branched DNA (bDNA), SDA, DNA and RNA chips, and arrays for gene expression and mutation analytics, differential display analytics, RFLP, AFLP, cDNA syntheses, subtractive hybridization, or the TaqMan technology and similar real-time quantification methods have been used in these tests.

In addition to stabilization, the present invention also relates to the isolation of nucleic acids.

In this context, the term "nucleic acid" is to be understood in its broadest sense, i.e., comprise ribonucleic acids (RNA) as well as deoxyribonucleic acids (DNA) with any length and configuration, such as double strand, single strand, circular and linear, branched, etc., as well as any possible subtype, such as monomeric nucleotides, oligomers, plasmids, viral and bacterial DNA and RNA, as well as genomic and non-genomic DNA and RNA from animal and plant cells or other eukaryotes, mRNA in processed and non-processed form, tRNA, hn-RNA, rRNA, cDNA, etc.

Stabilization and isolation are two important steps in a reaction cascade representing an analysis based on nucleic acids. Said cascade might be depicted schematically as follows:

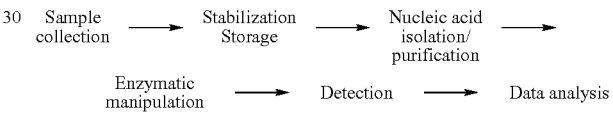

The present invention deals with the highlighted steps of the above cascade.

There is a number of methods of isolating nucleic acids where the cell is destroyed and RNA and/or DNA is liberated into solution. As a rule, well-known procedures of isolating nucleic acids from complex materials such as blood, serum, urine, or feces comprise lysis of the biological material by means of a detergent in the presence of proteinases, followed by multiple extractions using organic solvents such as phenol and/or chloroform, ethanol precipitation, and dialysis of the nucleic acids. Procedures of this type have been described by e.g. Chirgwin et al., Biochem. 18, 5294-5299 (1979), D. M. Wallace in Meth. Enzym. 152, 33-41 (1987), P. Chomczynski and N. Sacchi, Anal. Biochem. 162, 156-159 (1987), and "Preparation and Analysis of RNA" in Current Protocols in Molecular Biology, Unit 4.2 (Supplement 14), editor: F. M. Ausubel et al., John Wiley (1991), T. Maniatis et al., Molecular Cloning, A Laboratory Manual, Cold Spring Harbour Laboratory (1992); L. G. Davis et al., "Guanidine Isothiocyanate Preparation of Total RNA" and "RNA Preparation: Mini Method" in Basic Methods in Molecular Biology, Elsevier, N.Y., pages 130-138 (1991), and in U.S. Pat. No. 4,843,155 to Chomczynski.

Furthermore, it is familiar to isolate nucleic acids from various starting materials by mixing the starting material with a chaotropic substance and a solid phase which binds the nucleic acid. In a subsequent step, the solid phase is separated from the liquid and washed. If necessary, the nucleic acids can be eluted from the solid phase (U.S. Pat. No. 5,234,809).

Frequently, these well-known methods of isolating nucleic acids from biological materials are exceedingly laborious and time-consuming. The number of steps—mostly being relatively large—required to purify the nucleic acids from such starting materials increases the risk of transferring nucleic acids from sample to sample when processing miscellaneous clinical samples at the same time. In case the nucleic acid is isolated for subsequent detection of the presence of nucleic acids of e.g. a pathogenic organism using a nucleic acid amplification procedure, e.g. for the highly sensitive polymerase chain reaction, the risk of such a transfer of nucleic acids between separate samples will result in wrong positives, which obviously represents a serious drawback.

In MacFarlane, U.S. Pat. No. 5,010,183, and MacFarlane, U.S. Pat. No. 5,300,635, methods of isolating nucleic acids using cationic detergents based on quaternary ammonium compounds have been described. All of the ammonium compounds protected in the above-mentioned patents have the general form $[N(R)_4]^+X^-$, wherein R represents various alkyl or aryl groups having varying numbers of C atoms, and X represents a counterion from the group of carboxylic acids, sulfate, phosphate or halide. Moreover, high g values are required to pelletize the complex of nucleic acid and detergent. While the isolation of nucleic acids using the above-described procedures is possible in principle, high amounts of carrier and high g values are necessary.

All of the examples described in the above-mentioned US patents relate to the extraction of nucleic acids from whole blood or cells (human and E. coli). A certain minimum quantity of nucleic acids is present in these sample materials. In some of the cases, additional tRNA has been added as carrier. Using the example of purifying small amounts (e.g. low numbers of copies in viral infections) of RNA from cell-free sample materials such as plasma, it has been possible to demonstrate—using the example of tetradecyltrimethylammonium oxalate—that complexing/pelletizing can only be achieved when using large amounts of carrier RNA (100 µg/ml of plasma). For example, such purification is necessary in the detection of viral RNA in plasma or serum samples. These high amounts of carrier present a problem in the subsequent detection of viral RNA using RT PCR, because reverse transcription is inhibited by high concentrations of carrier. Also, MacFarlane as well describes a lower sensitivity in the detection of HCV in plasma (with no carrier) as compared to blood (Schmidt et al. J. Med. Virol. 47, 153-160 (1995)). In the absence of high amounts of nucleic acid, the sensitivity is very poor. In U.S. Pat. No. 5,300,635, MacFarlane also describes the sedimentation of RNA-detergent complexes by centrifuging at high g values (16,000×g in Examples 4, 5 and 6). Also, it has been demonstrated that centrifugation at low g values is not sufficient to sediment RNA-tetradecyltrimethylammonium oxalate complexes from plasma. In order to purify viral RNA from large volumes of plasma or serum (>1 ml), it is absolutely necessary to achieve sedimentation of the nucleic acid-detergent complexes at low g values because otherwise, costly and complex ultracentrifuges must be used instead of simple laboratory centrifuges (having a maximum achievable g values of 5,000-6,000).

In the embodiments in U.S. Pat. No. 5,300,635, MacFarlane describes the addition of at least 2 volumes and up to 10 volumes of detergent to the sample. Thus, the total volume to be processed is considerably increased in some cases, particularly when reflecting the purification of nucleic acids from several milliliters of sample material (e.g. plasma pools). However, processing large volumes is unfavorable, particularly with respect to an optional automatization of sample preparation on a pipetting robot because the pipetted volumes are limited, for example.

Therefore, a method of stabilizing and/or isolating nucleic acids is required that would not involve the above-mentioned drawbacks of prior art.

More specifically, a method is required which permits stabilization of nucleic acids and/or lysis of a sample containing the nucleic acids and isolation of the nucleic acids from the same solution in a single step. For example, this is important if nucleic acids are to be stabilized/isolated from such samples wherein induction of stress genes and thus, synthesis of new m-RNA molecules may occur upon extraction of the sample, so that the transcript pattern of the cells might be changed. In particular, a method is also required wherein complexes consisting of nucleic acid and cationic compounds can be sedimented at low g values. Furthermore, a method is particularly required that would necessitate only low amounts of carrier nucleic acids or carrier aids such as heparin, or even none at all. In addition, a method is required allowing addition of smaller volumes of cationic compound to the sample. Finally, a method is required that would allow operation in small volumes even after the first processing step.

These objects are accomplished by means of the following methods, compositions, and kits:

(1) A method of stabilizing and/or isolating nucleic acids from a biological sample, comprising D the following step:

contacting the biological sample with at least one cationic compound of formula (I)

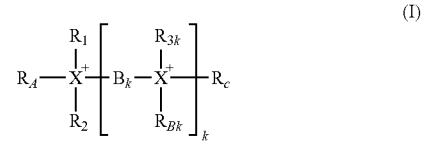

wherein conjugated bases of strong and/or weak inorganic and/or organic acids are used as anion (A), and wherein the substance consisting of (I) and the anion is neutral in charge on the whole, and wherein X represents nitrogen (N) or phosphorus (P), k represents the integer 1, 2, 3, 4, 5, 6, 7, 8, 9, 10, 11, 12, 13, 14, 15, 16, 17, 18, 19, 20, 21, 22, 23, or 24, $B_k$ represents aliphatic alkanediyl bridges, which may be substituted on none, on one or more carbon atoms, and wherein one or more non-adjacent carbon atoms may be replaced by oxygen, and which have the structure

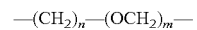

wherein n and m independently represent the integer 0, 1, 2, 3, 4, 5, or 6, with n+m>0; alternatively, $B_k$ represents a substituted phenyl, naphthyl or biphenyl bridge, which, in addition, may be substituted on one or more carbon atoms and has the structure

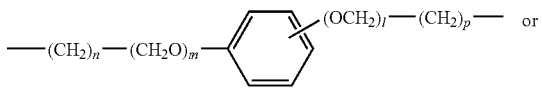 or

-continued

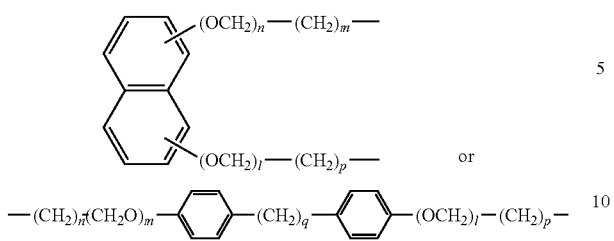

or

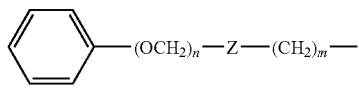

wherein n, m, l, p, q independently represent the integer 0, 1, 2, 3, 4, 5, or 6;

$R_1$, $R_2$, $R_{3k}$, which may be identical or different and which may be unsubstituted or substituted on one or more carbon atoms, represent hydrogen, linear or branched $C_1$-$C_6$ alkyl, linear or branched $C_1$-$C_6$ alkenyl, linear or branched $C_1$-$C_6$ alkynyl, phenyl, benzyl, and phenoxyethyl having the structure

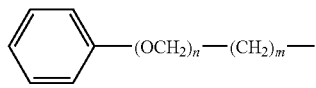

wherein n, m independently represent the integer 0, 1, 2, 3, 4, 5, or 6, and

Z represents one of the structures —O—, —CO—, —CO$_2$—, —OCO—, —CO—N—, —N—CO—, —O—CO—N—, —N—CO—O—, —S—, or —S—S—;

or $R_1$, $R_2$, $R_{3k}$ represent phenyl, benzyl, phenoxyethyl having the structure

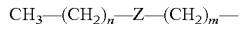

wherein n, m independently represent the integer 0, 1, 2, 3, 4, 5, or 6;

$R_A$, $R_{Bk}$, $R_C$, which may be identical or different and which may be unsubstituted or substituted on one or more carbon atoms, represent hydrogen, linear or branched $C_1$-$C_{21}$ alkyl, linear or branched $C_1$-$C_{21}$ alkenyl, linear or branched $C_1$-$C_{21}$ alkynyl, and a structure $CH_3$—$(CH_2)_n$—Z—$(CH_2)_m$— wherein n, m independently represent the integer 0, 1, 2, 3, 4, 5, 6, 7, 8, 9, 10, 11, 12, 13, 14, 15, 16, 17, 18, 19, 20, 21, 22, 23, or 24, and Z represents —O—, —CO—, —CO$_2$—, —OCO—, —CO—N—, —N—CO—, —O—CO—N—, —N—CO—O—, —S—, or —S—S—;

alternatively, $R_A$ and $R_C$ together form a residue $R_{AC}$ having a cyclic structure

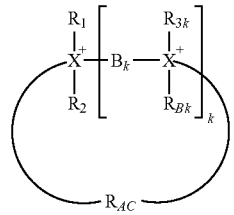

wherein the residue $R_{AC}$, which may be unsubstituted or substituted on one or more carbon atoms, represents linear or branched $C_1$-$C_8$ alkyl, linear or branched $C_1$-$C_8$ alkenyl, or linear or branched $C_1$-$C_8$ alkynyl, and if k>1, the bridging groups $B_k$ and the groups $R_{Bk}$ and $R_{3k}$ are the same or different;

(2) A kit for stabilizing and/or isolating nucleic acids, comprising at least one cationic compound as defined above by formula (I);

(3) A complex, comprising a nucleic acid and at least one cationic compound, formed as the result of the method in (1);

(4) A composition of matter, comprising at least one cationic compound as defined above by formula (I);

(5) A pharmaceutical composition, comprising the composition of matter in (4);

(6) A diagnostic composition, comprising the composition of matter in (4); and (7) A composition for research, comprising the composition of matter in (4).

The intention is to provide a method of stabilizing and/or isolating nucleic acids from a biological sample. According to the invention, this object is accomplished by means of the method of stabilizing and/or isolating nucleic acids from a biological sample in accordance with the method according to (1) above, the kit for stabilizing and/or isolating nucleic acids according to (2) above, the complex according to (3) above, the pharmaceutical composition according to (5) above, the diagnostic composition according to (6) above, the composition for research in accordance with (7) above, and the cationic compound according to formula (I).

According to the invention, a biological sample is contacted with at least one cationic compound of formula (I) in order to stabilize and/or isolate nucleic acids:

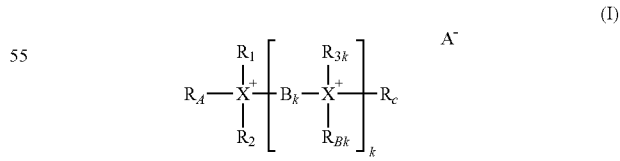

Within the scope of the present invention, the term "cationic compound" is understood to indicate a compound having more than one positive charge. The cationic compound depicted as formula (I) is used in a dissolved form and/or in the form of a salt, with charge neutralization being effected by the conjugated bases of strong and/or weak inorganic and/or organic acids, which will be abbreviated as "A" hereinafter.

Consequently, the product of charge and number of bases will exactly compensate the positive charges of the rest of the compound.

In the above formula (I), X represents nitrogen atoms (N) or phosphor atoms (P). In formula (Ia), the cationic compound is shown were X=N, and in formula (Ib) the cationic compound is shown were X=P.

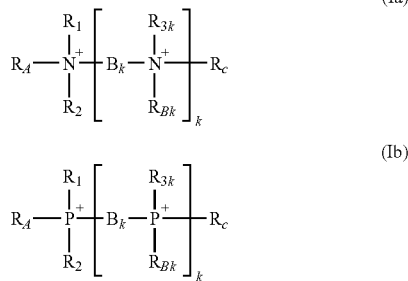

In addition, k represents the integer 1, 2, 3, 4, 5, 6, 7, 8, 9, 10, 11, 12, 13, 14, 15, 16, 17, 18, 19, 20, 21, 22, 23, or 24, while $B_k$ represents aliphatic alkanediyl bridges wherein one or more non-adjacent carbon atoms may be replaced oxygen, and which have the structure

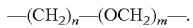

Within the scope of the present invention, the alkanediyl bridges may be substituted on one or more carbon atoms. The parameters n and m are independent of each other and represent one of the integers 0, 1, 2, 3, 4, 5, or 6, with n+m>0.

As an alternative to the above-specified structures, $B_k$ also represents a substituted phenyl, naphthyl or biphenyl bridge having the structure

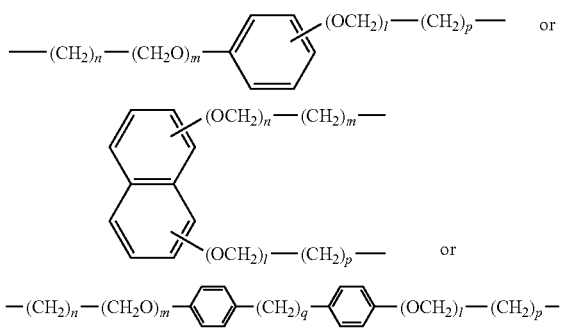

wherein n, m, l, p, q are independent of each other and represent one of the integers 0, 1, 2, 3, 4, 5, or 6. In addition, the phenyl, naphthyl or biphenyl bridge may be substituted on one or more carbon atoms.

In addition, $R_1$, $R_2$, $R_{3k}$ in formula (I) illustrated above, which may be identical or different and which may be unsubstituted or substituted on one or more carbon atoms, represent hydrogen, linear or branched $C_1$-$C_6$ alkyl, linear or branched $C_1$-$C_6$ alkenyl, linear or branched $C_1$-$C_6$ alkynyl, phenyl, benzyl, phenoxyethyl having the structure

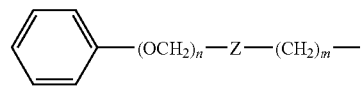

wherein n, m independently represent the integers 0, 1, 2, 3, 4, 5, or 6, and Z represents one of the structures —O—, —CO—, —CO$_2$—, —OCO—, —CO—N—, —N—CO—, —O—CO—N—, —N—CO—O—, —S—, or —S—S—.

Moreover, $R_1$, $R_2$, $R_{3k}$ may represent phenyl, benzyl, phenoxyethyl having the structure

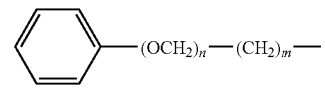

wherein n, m independently represent the integers 0, 1, 2, 3, 4, 5, or 6.

$R_A$, $R_{Bk}$, $R_C$, which may be identical or different and which may be unsubstituted or substituted on one or more carbon atoms, represent hydrogen, linear or branched $C_1$-$C_{21}$ alkyl, linear or branched $C_1$-$C_{21}$ alkenyl, linear or branched $C_1$-$C_{21}$ alkynyl, or a structure

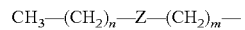

wherein n, m independently represent the integers 0, 1, 2, 3, 4, 5, 6, 7, 8, 9, 10, 11, 12, 13, 14, 15, 16, 17, 18, 19, 20, 21, 22, 23, or 24, and Z represents one of the structures —O—, —CO—, —CO$_2$—, —OCO—, —CO—N—, —N—CO—, —O—CO—N—, —N—CO—O—, —S—, or —S—S—.

Alternatively, $R_A$ and $R_C$ together form a rest $R_{AC}$ and thus, a cyclic structure

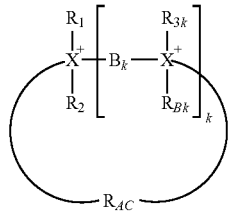

wherein the residue $R_{AC}$, which may be unsubstituted or substituted on one or more carbon atoms, represents linear or branched $C_1$-$C_8$ alkyl, linear or branched $C_1$-$C_8$ alkenyl, or linear or branched $C_1$-$C_8$ alkynyl.

If k>1, the bridging groups $B_k$ and the groups $R_{Bk}$ and $R_{3k}$ may be the same or different.

The compounds specified above are used in the method of the invention, thereby allowing stabilization of nucleic acids, lysis of the sample containing the nucleic acids, and/or isolation of the nucleic acids in one single step. The stabilized nucleic acids not only are stable during the preparation but also over a prolonged period of time, such as 96 hours or more. In particular, the complexes consisting of nucleic acid and cationic compound can be sedimented at low g values, where only low amounts of carrier nucleic acids or carrier aids are required, or even none at all, and where only small volumes or amounts of cationic compound must be added to the sample. In addition, owing to the pelletizing of the complexes, it is possible to work in small volumes as early as after this step.

As a result of the inventive stabilization of nucleic acids, the nucleic acids in a sample do not change their structure even upon prolonged storage or during transportation, and the accuracy of tests to be conducted at a later time is significantly increased. In some cases, e.g. where materials containing nucleic acids have to be shipped over long distances or subjected to prolonged storage, such tests are actually made possible by the method of the invention.

The compound may be added in solution or as a solid. The option of adding as a solid involves the additional advantages that solids mostly have higher chemical stability and their addition to the sample frequently can be done more easily. It is possible to add one cationic compound or a mixture of two or more cationic compounds.

The method according to the invention preferably uses compounds of general formula (I) specified above, where an anion A selected from the group of fluoride, chloride, bromide, iodide, perchlorate, perbromate, periodate, phosphate, hydrogen phosphate, dihydrogen phosphate, sulfate, thiosulfate, hydroxide, carboxylic acids, α-halocarboxylic acids, and/or hydroxycarboxylic acids is used, and k represents the integer 1, 2, 3, 4, 5, or 6, while in that case where $B_k$ represents a substituted phenyl, naphthyl or biphenyl bridge, n, m, l, p, q independently represent the integers 0, 1 or 2.

In the compounds of general formula (I) which are preferred according to the invention, the residues $R_1$, $R_2$ and $R_{3k}$, which may be identical or different, represent the $C_1$-$C_6$ alkyl groups methyl, ethyl, propyl, isopropyl, butyl, 1-methylpropyl, 2-methylpropyl, 1,1-dimethylethyl, n-pentyl, 1-methylbutyl, 2-methylbutyl, 3-methylbutyl, 1,1-dimethyl-propyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and/or 1-ethyl-2-methyl-propyl, and/or the $C_3$-$C_6$ alkenyl groups 2-propenyl (allyl), 2-butenyl, 3-butenyl, 1-methyl-2-propenyl, 2-methyl-2-propenyl, 2-pentyl, 3-pentyl, 4-pentyl, 1-methyl-2-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-ethyl-2-butenyl, 2-ethyl-3-butenyl, 1,1,2-trimethyl-2-propenyl, 1-ethyl-1-methyl-2-propenyl, and/or 1-ethyl-2-methyl-2-propenyl, and/or the $C_3$-$C_6$ alkynyl groups 2-propynyl (propargyl), 2-butynyl, 3-butynyl, 2-pentynyl, 3-pentynyl, 4-pentynyl, 3-methyl-2-butynyl, 2-hexynyl, 3-hexynyl, 4-hexynyl, 5-hexynyl, 3-methyl-2-pentynyl, 4-methyl-2-pentynyl, 2-methyl-3-pentynyl, 4-methyl-3-pentynyl, 1-methyl-4-pentynyl, 1,1-dimethyl-2-butynyl, 1,1-dimethyl-2-butynyl, 1,1-dimethyl-3-butynyl, 1,2-dimethyl-3-butynyl, 1,3-dimethyl-2-butynyl, 2,2-dimethyl-3-butynyl, 1-ethyl-2-butynyl, 1-ethyl-3-butynyl, 2-ethyl-3-butynyl, and/or 1-ethyl-1-methyl-2-propynyl, and/or the groups benzyl, phenylethyl, phenylpropyl, phenylisopropyl, phenylisobutyl, phenoxymethyl, phenoxyethyl, phenoxypropyl, phenoxyisopropyl, phenoxybutyl, phenoxyisobutyl having the structure

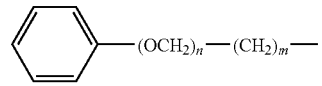

wherein n, m independently represent the integers 0, 1 or 2.

The residues $R_A$, $R_{Bk}$, $R_C$, which may be identical or different, represent the linear or branched $C_8$-$C_{20}$ alkyl groups octyl, decyl, undecyl, dodecyl, tridecyl, tetradecyl, pentadecyl, hexadecyl, heptadecyl, octadecyl, nonadecyl, and/or eicosyl, and/or the linear or branched $C_8$-$C_{20}$ alkenyl groups octenyl, decenyl, undecenyl, dodecenyl, tridecenyl, tetradecenyl, pentadecenyl, hexadecenyl, heptadecenyl, octadecenyl, nonadecenyl, and/or eicosenyl, and/or the linear or branched $C_8$-$C_{20}$ alkynyl groups octynyl, decynyl, undecynyl, dodecynyl, tridecynyl, tetradecynyl, pentadecynyl, hexadecynyl, heptadecynyl, octadecynyl, nonadecynyl, and/or eicosynyl, and/or a structure

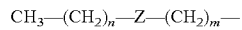

wherein n, m are independent of each other, and n represents the integer 2, 3 or 4, m represents the integer 8, 9, 10, 11, 12, 13, 14, 15, 16, 17, or 18, and Z represents one of the structures —O—, —CO—, —OCO—, —CO—N—, or —N—CO—.

Within the scope of the present invention, it is preferred to use compounds of general formula (I) wherein one or more of the groups designated as $R_A$, $R_{Bk}$ and $R_C$ represent one of the structures

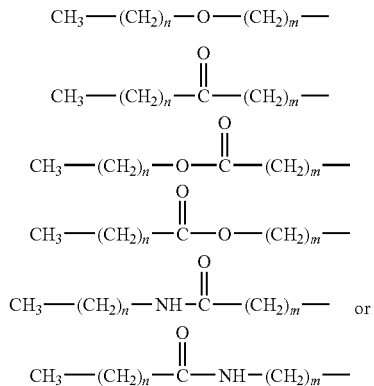

Among the above-mentioned compounds preferred according to the invention, those compounds are particularly preferred wherein one or more residues $R_1$, $R_2$, $R_{3k}$, $R_A$, $R_{Bk}$, and $R_C$ have a double bond or a triple bond.

In particular, those compounds are preferred wherein an allyl group is used as residue $R_1$, $R_2$ and/or $R_{3k}$.

Within the scope of the present invention, it is particularly preferred to use compounds of the above-specified general formula (I) where an anion A is employed, selected from the group of bromide, iodide, perchlorate, hydrogen phosphate, sulfate, acetate, trifluoroacetate, trichloroacetate, benzoate, oxalate, succinate, phthalate, citrate, tartrate, maleate, malonate, fumarate. Furthermore, k represents the integer 1 or 2, while $B_k$ represents the aliphatic $C_2$-$C_4$ alkanediyl bridges ethane-1,1-diyl, ethane-1,2-diyl, propane-1,1-diyl, propane-1,2-diyl, propane-1,3-diyl, butane-1,1-diyl, butane-1,2-diyl, butane-1,3-diyl, and/or butane-1,4-diyl. $R_1$, $R_2$, $R_{3k}$ represent methyl, ethyl or hydroxyethyl, while $R_A$, $R_{Bk}$, $R_C$ represents the linear $C_8$-$C_{20}$ alkyl groups octyl, decyl, undecyl, dodecyl, tridecyl, tetradecyl, pentadecyl, hexadecyl, heptadecyl, octadecyl, nonadecyl, and/or eicosyl.

In the method according to the invention, it is particularly preferred to use compounds of general formula (I) wherein the residues $R_1$, $R_2$ and $R_{3k}$ are identical and/or $R_A$, $R_{Bk}$ and $R_C$ are identical and/or if k>1, the bridging groups $B_k$ are identical.

In all the compounds used according to the invention, the carbon atoms in the groups $R_1$, $R_2$, $R_{3k}$, $R_A$, $R_{Bk}$, and $R_C$ may be substituted with one or more halogen atoms, particularly one or more fluorine atoms, and/or one or more primary, secondary and/or tertiary hydroxyl groups, and/or one or more —SH, —$NH_2$, —NH—, and/or =N— groups, where the substituents may be identical or non-identical to each other. Those compounds are preferred wherein the distance between the first substituted carbon atom and the nitrogen drawn in general formula (I) is at least two covalent bonds. As a consequence, one or more carbon atoms of the groups $R_1$, $R_2$, $R_{3k}$, $R_A$, $R_{Bk}$, and $R_C$, which are not directly bound to one of the atoms (nitrogen or phosphor) in compound

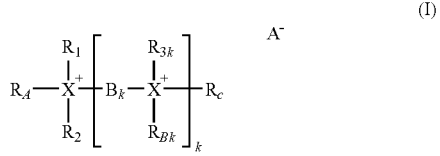

are substituted.

In all the embodiments, the aliphatic and/or aromatic carbon atoms of the bridging groups $B_k$ may likewise be substituted with one or more halogen atoms, particularly fluorine atoms, and/or one or more primary, secondary and/or tertiary hydroxyl groups, and/or one or more —SH, —$NH_2$, —NH— and/or =N— groups, and/or one or more linear or branched $C_1$-$C_4$ alkyl groups, where the substituents may be identical or non-identical to each other. In particular, methyl, ethyl, propyl, i-propyl, butyl, 2-methylpropyl, and tert-butyl groups are preferred as substituents on the carbon atoms of the bridging groups $B_k$.

It is particularly preferred to perform the method of the invention using the cationic compounds ethanediyl-1,2-bis(dimethyldecylammonium bromide), propanediyl-1,2-bis(dimethyldecylammonium bromide), ethanediyl-1,2-bis(dimethyltetradecylammonium bromide), or N,N',N''-tridecyl-N,N,N',N'',N''-pentamethylbis(2-ammonioethyl)ammonium bromide.

As has been mentioned, said at least one cationic compound can be added to the sample both as a solid and in a dissolved form. If the cationic compound is added in solution, from 0.001 to 10 volumes, preferably from 0.01 to 10 volumes, more preferably from 0.05 to 2 volumes, and most preferably 1 volume of solution is added to the sample, i.e., significantly smaller amounts than those known from prior art. Larger or smaller volumes are also possible, if practical advantages result. The solution of the cationic compound has a concentration of from 0.01% to saturation, preferably from 0.5 to 5%, and more preferably from 2 to 4%.

Of course, the biological sample may be subjected to a primary purification prior to contacting, if advantageous for further processing.

After contacting the cationic compound with a biological sample, the cationic compound can be mixed with the biological sample, and the mixture can be incubated, incubation preferably being performed for 10 minutes at room temperature.

According to a preferred embodiment of the present invention, the cationic compound and/or the complex formed of nucleic acid and cationic compound may be added with additional means to support lysis. Alcohols, particularly branched and unbranched C1- to C4-alkanols like isopropanol, aldehydes particularly lower C1- to C4-aldehydes, branched or unbranched such as glyoxal, phenols, phenol derivatives such as 2-biphenylol, ionic, zwitterionic and non-ionic compounds, reagents reducing sulfhydryl, particularly dithiothreitol, phosphoric acid derivatives, particularly tributyl phosphate, chaotropic reagents such as urea, carboxylic acids, such as citric acid or malonic acid, or plain salts, such as ammonium salts or alkali phosphates, can be used alone or in combination as agents to support lysis.

According to another preferred embodiment of the present invention, it is also possible to homogenize the biological sample or subject it to mechanical or enzymatic exposure prior to or during addition of the cationic compound. For example, mechanical exposure might be effected using an electric knife, a ball mill, addition of particles, or by pressing through a syringe, while suitable enzymes to act upon the sample might be hydrolases, proteases or lipases, for example. Other options are well-known to those skilled in the art and are encompassed herein. Such treatment of a biological sample might be advantageous in that the cationic compound has a better chance of contacting its targets of attack.

According to the invention, the complexes formed of nucleic acid and cationic compound are sedimented by centrifuging. Centrifugation preferably is conducted at low g values, particularly from 500 to 5000×g for 3-10 minutes. Owing to the sedimentation of the complex into a small pellet, it is possible to perform further purification of the nucleic acids in relatively small volumes. This is particularly advantageous in routine uses, and especially in automatized procedures. Centrifugation at low g values permits the use of simple laboratory centrifuges.

Optionally, the complexes subsequently may be washed with a suitable buffer or with water, thereby allowing removal of impurities. The complexes consisting of cationic compound and nucleic acids are then redissolved in a relatively small volume of a suitable buffer, thereby liberating the nucleic acids into the buffer. If necessary, the nucleic acids may then be subjected to further purification in relatively small volumes, using various well-known procedures. Thus, following adjustment of appropriate binding conditions, they might be bound to a membrane for further purification, for example. As an alternative to removal by centrifugation, the complexes of nucleic acid and cationic compound may be concentrated using a vacuum, excess pressure, centrifugation, or capillary forces on a surface, e.g. the surface of a membrane, or on the bottom of a vessel. Optionally, the complexes may then be washed in a suitable washing solution, thereby removing impurities in an advantageous fashion. Subsequently, the complexes can be dissolved by adding a suitable reagent solution, optionally including an enzyme, and/or by mechanical exposure under binding or non-binding conditions, thereby liberating the nucleic acids into the solution. If dissolved under binding conditions, the nucleic acids can be bound e.g. on the same membrane as above, using centrifugation, vacuum, excess pressure, or capillary forces (such methods have been described e.g. in the PCT application No. PCT/EP98/06756 and are hereby incorporated by reference), and subjected to further purification. If the complexes are dissolved under non-binding conditions, the nucleic acids can be collected in a collecting tube by means of centrifugation, vacuum, or excess pressure. If necessary, they may then be subjected to further purification in relatively small volumes, using various well-known procedures. Thus, for example, it is obviously possible—once appropriate binding conditions have been adjusted—to rebind them on a membrane or another surface for further purification.

Sample materials free of cells, food samples containing free or bound nucleic acids or nucleic acid-containing cells, environmental samples containing free or bound nucleic acids or nucleic acid-containing cells, suspensions of cells, bacteria, viruses, or yeasts, any type of tissue or clinical samples such as blood, plasma, serum, leukocyte fractions, *Crusta phlogistica*, sputum, urine, sperm, feces, or smears, as well as plants or plant parts or free nucleic acids can be used as biological samples including nucleic acids, as well as any other imaginable sample which contains nucleic acids.

According to the invention, the above-specified cationic compounds are used in a kit for stabilizing and/or isolating nucleic acids, which kit preferably includes additional suitable buffers. In addition, the kit may include suitable means to support lysis and/or means for purifying the nucleic acids and/or means for mechanical exposure and/or means for enzymatic treatment of the samples and/or complexes.

According to the invention, the above-specified cationic compounds are used to stabilize and/or isolate nucleic acids, a complex being formed which consists of a nucleic acid and a cationic compound. Said complex is remarkable for its particularly advantageous, high stability, thereby protecting nucleic acids from being degraded in the sample itself or by environmental exposure.

According to the invention, the above-specified cationic compounds or complexes find use in pharmaceutical compositions, diagnostic compositions—said diagnostic compositions being intended to encompass both the diagnostics in the medical-pharmaceutical field and the examination of food and environmental samples—as well as in compositions for research. For example, the generated stabilized complex of nucleic acid and cationic compound might be used advantageously for the inward transfer of pharmaceutically effective NA into diseased cells.

The items claimed within the scope of the present invention also include all of the above-specified cationic compounds.

The method of the invention can be used in a simple fashion to automatize the stabilization and/or isolation of nucleic acids. Each one of the advantages of the method according to the invention, namely, stabilization of the nucleic acids, lysis of the sample containing the nucleic acids in one single step and/or isolation of the nucleic acids from the same solution, sedimentation of the complexes consisting of nucleic acid and cationic compound at low g values, use of low quantities of carrier nucleic acids or carrier aids or even no carrier nucleic acids or carrier aids at all, as well as small volumes of cationic compound and small sample volumes after pelletizing, contributes to facilitated automatization, and all the more so, in combinations with each other. Operations may also be performed e.g. in a multi-well module such as an 8-well or a 96-well module.

The present invention will be illustrated in more detail with reference to the following embodiments.

Linear, branched and cyclic cationic compounds are prepared according to Examples 1 or 2. To bind the residues $R_A$ and $R_{Bk}$ (if k=1, $R_C$ will be used instead of $R_{Bk}$) to the nitrogen atoms by nucleophilic substitution, tertiary diamines or tertiary polyamines (k>1) having a predetermined number of tertiary nitrogen atoms were added with an excess of alkyl halide in solution under argon protective gas. The nitrogen atoms are linked by linear (unbranched) alkanediyl bridges or substituted xylylene bridges having the appropriate length n. This per se known quaternization reaction was conducted at elevated temperatures. Alkyl halides such as alkyl bromide or alkyl iodide were used in excess to prepare ammonium salts, most of which were completely quaternized. The ammonium compounds thus obtained were purified by recrystallization from various solvents and solvent mixtures such as diethyl ether/methanol.

Alternatively, cationic compounds having two cationic nitrogen atoms (k=1) were synthesized. To this end, primary α,ω-alkanyl dihalides were reacted with an excess of alkyldimethylamine under the reaction conditions according to Example 1. The alkyl chain of the amine compound may be hydroxylated but has no halogen atoms. The cationic compounds are purified as described above.

The counterions (anions A) can be exchanged using an ion exchange column. Example 3 exemplifies the exchange of bromide for acetate.

EXAMPLE 1

Synthesis of ethanediyl-1,2-bis(dimethyldecylammonium bromide)

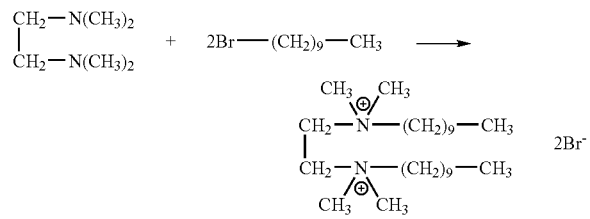

In a 2 l round-bottom flask equipped with reflux condenser, heating jacket and magnetic stirrer, a solution of 46.0 ml of N,N,N',N'-tetramethylethylenediamine (35.4 g, 0.30 mol) and 151.4 ml of 1-bromodecane (161.8 g, 0.73 mol, 20% excess) in 850 ml of acetonitrile and 280 ml of acetone was heated for 42 hours at reflux temperature. Thereafter, the reaction mixture was cooled to room temperature and then ice-cooled in order to complete crystallization of the reaction products. The crystal mass then was suction-filtered and washed twice with a total of 200 ml of cold acetone. The solid reaction product then was transferred into a 2 l round-bottom flask equipped with reflux condenser, and added with 1.8 l of diethyl ether. Once reflux temperature had been reached, small amounts of methanol were added until the solid had completely dissolved. To this end, a total of about 350 ml of methanol was added. The product crystallized overnight at 4° C. and was then suction-filtered and dried in a vacuum drying oven at 60° C. The first fraction gave 102 g of dry product (60% of theoretical yield). A second fraction of the reaction batch gave 1.8 g of dry product after recrystallization. A TLC analysis of the dry product (Silica RP18 plate; mobile phase: chloroform 25%, methanol 16%, n-propanol 25%, ethyl acetate 25%, 0.25% aqueous potassium chloride solution 9%) showed a new substance spot after staining in an iodine chamber. There were no educts present anymore.

The cyclic compounds, i.e., those compounds where the residues $R_A$ and $R_C$ together form a residue $R_{AC}$, were prepared in analogy to the preparation of ethanediyl-1,2-bis (dimethyldecylammonium bromide) described above. The reaction equation of the preparation of N,N'-dioctadecyl-N,N'-dimethylpiperazine-diium dibromide from 1,4-dimethylpiperazine and octadecyl bromide is given as an example:

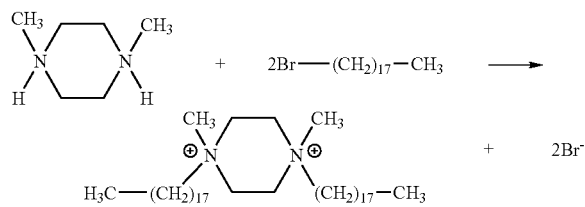

EXAMPLE 2

Synthesis of N,N',N''-tritetradecyl-N,N,N',N'',N''-pentamethyl-bis(2-ammonioethyl)ammonium bromide

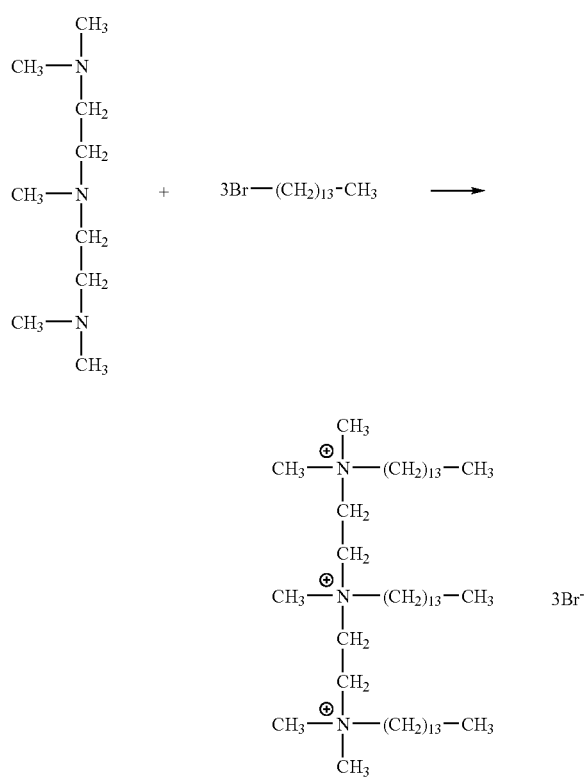

In a 2 l round-bottom flask equipped with reflux condenser, heating jacket and magnetic stirrer, a solution of 20.9 ml of N,N,N',N',N''-pentamethyldiethylenetriamine (17.3 g, 0.10 mol) and 93.5 ml of 1-bromotetradecane (99.8 g, 0.36 mol, 20% excess) in 500 ml of acetonitrile and 150 ml of acetone was heated to reflux temperature for 72 hours.

Thereafter, the reaction mixture was cooled to room temperature and stored at 4° C. overnight in order to complete crystallization of the reaction products. The crystallized solid then was suction-filtered and washed twice with a total of 200 ml of cold acetone. The solid was transferred into a 1 l round bottom flask equipped with reflux condenser, added with 1.8 l of diethyl ether and heated to reflux. 250 ml of methanol was added in order to completely dissolve the solid. The solution then was cooled to room temperature and stored at 4° C. overnight. The precipitated product was filtrated and dried in a vacuum drying oven at 60° C. The yield was 60.1 g (59% of theoretical yield). Following recrystallization, another 3.1 g of product was obtained from the filtrate of the original reaction batch. After staining in an iodine chamber, TLC analysis (Silica RP18 thin layer plate; mobile phase: chloroform 25%, methanol 16%, n-propanol 25%, ethyl acetate 25%, 0.25% aqueous potassium chloride solution 9%) showed a new spot. Educts could not be detected anymore.

EXAMPLE 3

Preparation of Cationic Compounds Using Acetate as Counteranion

A chromatographic column was packed with 8 g of Dowex® 1×8-400 anion exchanger. Using 50% aqueous methanol, the column was washed thoroughly until the eluate was color-less. The column then was loaded with a total of 20 column volumes of a 1 M acetic acid, washed with distilled water to neutrality, and finally washed with 10 column volumes of 50% aqueous methanol. Following these washing steps, a solution of 1 g of cationic compound in the form of its bromide in 2 ml of 50% aqueous methanol was applied on the column at a flow rate of 1 ml/min. Using 50% aqueous methanol, the compound was eluted in 15 column volumes. The product was isolated from the eluate using freeze-drying.

According to the reactions specified as Example 1, the following compounds were prepared, all of them were recrystallized from diethyl ether/methanol:

| Educts | | Reaction time | Yield | Product |
| --- | --- | --- | --- | --- |
| Tetramethylethylenediamine | Octyl bromide | 42 hours | 45% | Ethanediyl-1,2-bis(octyldimethyl-ammonium bromide) |
| Tetramethylethylenediamine | Decyl bromide | 42 hours | 65% | Ethanediyl-1,2-bis(decyldimethyl-ammonium bromide) |
| Tetramethylethylenediamine | Dodecyl bromide | 42 hours | 63% | Ethanediyl-1,2-bis(dodecyldimethyl-ammonium bromide) |

-continued

| Educts | | Reaction time | Yield | Product |
|---|---|---|---|---|
| Tetramethylethylenediamine | Tetradecyl bromide | 42 hours | 35% | Ethanediyl-1,2-bis(tetradecyldimethyl-ammonium bromide) |
| Tetramethylethylenediamine | Hexadecyl bromide | 42 hours | 41% | Ethanediyl-1,2-bis(hexadecyldimethyl-ammonium bromide) |
| Tetramethylethylenediamine | Octadecyl bromide | 42 hours | 14% | Ethanediyl-1,2-bis(octadecyldimethyl-ammonium bromide) |
| 1,4-Dimethylpiperazine | Octadecyl bromide | 42 hours | 42% | N,N'-Dioctadecyl-N,N'-dimethylpiperazine-diium dibromide |
| Tetramethylpropanediamine | Decyl bromide | 42 hours | 77% | Propanediyl-1,3-bis(decyldimethyl-ammonium bromide) |
| Tetramethylpropanediamine | Dodecyl bromide | 42 hours | 85% | Propanediyl-1,3-bis(dodecyldimethyl-ammonium bromide) |
| Tetramethylpropanediamine | Tetradecyl bromide | 42 hours | 55% | Propanediyl-1,3-bis(tetradecyldimethyl-ammonium bromide) |
| Tetramethylpropanediamine | Hexadecyl bromide | 42 hours | 91% | Propanediyl-1,3-bis(hexadecyldimethyl-ammonium bromide) |
| Tetramethylpropanediamine | Octadecyl bromide | 42 hours | 87% | Propanediyl-1,3-bis(octadecyldimethyl-ammonium bromide) |
| Tetramethylbutanediamine | 1-Bromo-3-methylbutane | 42 hours | 98% | Ethanediyl-1,2-bis(3-methylbutyldimethyl-ammonium bromide) |
| Tetramethylbutanediamine | Decyl bromide | 42 hours | 78% | Butanediyl-1,4-bis(decyldimethyl-ammonium bromide) |
| Tetramethylbutanediamine | Dodecyl bromide | 42 hours | 82% | Butanediyl-1,4-bis(dodecyldimethyl-ammonium bromide) |
| Tetramethylbutanediamine | Tetradecyl bromide | 42 hours | 58% | Butanediyl-1,4-bis(tetradecyldimethyl-ammonium bromide) |
| Tetramethylbutanediamine | Hexadecyl bromide | 42 hours | 50% | Butanediyl-1,4-bis(hexadecyldimethyl-ammonium bromide) |
| Tetramethylbutanediamine | Octadecyl bromide | 42 hours | 32% | Butanediyl-1,4-bis(octadecyldimethyl-ammonium bromide) |
| Tetramethylbutanediamine | Elcosyl bromide | 42 hours | 72% | Butanediyl-1,4-bis(eicosyldimethyl-ammonium bromide) |
| Pentamethyldiethylenetriamine | Octyl bromide | 42 hours | 13% | N,N',N''-Trioctyl-N,N,N',N'',N''-pentamethyl-bis(2-ammonioethyl)ammonium bromide |
| Pentamethyldiethylenetriamine | Decyl bromide | 42 hours | 53% | N,N',N''-Tridecyl-N,N,N',N'',N''-pentamethyl-bis(2-ammonioethyl)ammonium bromide |
| Pentamethyldiethylenetriamine | Dodecyl bromide | 42 hours | 42% | N,N',N''-Triodecyl-N,N,N',N'',N''-pentamethyl-bis(2-ammonioethyl)ammonium bromide |
| Pentamethyldiethylenetriamine | Tetradecyl bromide | 42 hours | 54% | N,N',N''-Tritetradecyl-N,N,N',N'',N''-pentamethyl-bis(2-ammonioethyl)ammonium bromide |
| Pentamethyldiethylenetriamine | Hexadecyl bromide | 42 hours | 58% | N,N',N''-Trihexadecyl-N,N,N',N'',N''-pentamethyl-bis(2-ammonioethyl)ammonium bromide |
| Pentamethyldiethylenetriamine | Octadecyl bromide | 42 hours | 30% | N,N',N''-Trioctadecyl-N,N,N',N'',N''-pentamethyl-bis(2-ammonioethyl)ammonium bromide |
| Pentamethyldiethylenetriamine | Elcosyl bromide | 42 hours | 38% | N,N',N''-Trieicosyl-N,N,N',N'',N''-pentamethyl-bis(2-ammonioethyl)ammonium bromide |

In accordance with the specified alternative, the following compounds were prepared, all of them were recrystallized from diethyl ether/methanol.

| Educts | | Reaction time | Yield | Product |
|---|---|---|---|---|
| 1,2-Dibromoethane | Decylamine | 48 hours | 53% | Ethanediyl-1,2-bis(decyldimethyl-ammonium bromide) |
| 1,2-Dibromoethane | Dodecylamine | 48 hours | 55% | Ethanediyl-1,2-bis(dodecyldimethyl-ammonium bromide) |
| 1,2-Dibromoethane | Tetradecylamine | 48 hours | 53% | Ethanediyl-1,2-bis(tetradecyldimethyl-ammonium bromide) |
| 1,2-Dibromoethane | Hexadecylamine | 48 hours | 50% | Ethanediyl-1,2-bis(hexacyldimethyl-ammonium bromide) |
| 1,2-Dibromoethane | Octadecylamine | 48 hours | 48% | Ethanediyl-1,2-bis(octadecyldimethyl-ammonium bromide) |

-continued

| Educts | | Reaction time | Yield | Product |
|---|---|---|---|---|
| 1,3-Dibromopropane | Decylamine | 48 hours | 68% | Propanediyl-1,3-bis(decyldimethyl-ammonium bromide) |
| 1,3-Dibromopropane | Dodecylamine | 48 hours | 65% | Propanediyl-1,3-bis(dodecyldimethyl-ammonium bromide) |
| 1,3-Dibromopropane | Tetradecylamine | 48 hours | 63% | Propanediyl-1,3-bis(tetradecyldimethyl-ammonium bromide) |
| 1,3-Dibromopropane | Hexadecylamine | 48 hours | 64% | Propanediyl-1,3-bis(hexadecyldimethyl-ammonium bromide) |
| 1,3-Dibromopropane | Octadecylamine | 48 hours | 60% | Propanediyl-1,3-bis(octadecyldimethyl-ammonium bromide) |
| 1,4-Dibromobutane | Decylamine | 48 hours | 65% | Butanediyl-1,4-bis(decyldimethyl-ammonium bromide) |
| 1,4-Dibromobutane | Dodecylamine | 48 hours | 66% | Butanediyl-1,4-bis(dodecyldimethyl-ammonium bromide) |
| 1,4-Dibromobutane | Tetradecylamine | 48 hours | 63% | Butanediyl-1,4-bis(tetradecyldimethyl-ammonium bromide) |
| 1,4-Dibromobutane | Hexadecylamine | 48 hours | 65% | Butanediyl-1,4-bis(hexadecyldimethyl-ammonium bromide) |
| 1,4-Dibromobutane | Octadecylamine | 48 hours | 60% | Butanediyl-1,4-bis(octadecyldimethyl-ammonium bromide) |

EXAMPLE 4

Reference Example

A radiolabelled in vitro transcript of the mouse Evx gene 4.5 kb in length was used as a model for the isolation of viral RNA from plasma. Radiolabelling was performed by incorporating $\alpha^{32}$P-UTP in the RNA transcript using T7 RNA polymerase.

Experiment A

Four volumes (560 μl) of a 3.6% solution of tetra-decyltrimethylammonium oxalate is added to 140 μl plasma in a 1.5 ml reaction vessel. Carrier RNA (poly A RNA having a length of 700 bases up to 7 kb) in varying amounts and radiolabelled transcript are placed in the cap of the reaction vessel. The cap of the reaction vessel is secured, the sample is mixed thoroughly and incubated for 10 min at room temperature. The complexes consisting of RNA and cationic compound are sedimented for 2 min at 10,000×g, the supernatant is removed, and the pellet is resuspended in 600 μl of a buffer containing guanidinium thiocyanate and added with 1 volume of 70% ethanol. The sample is applied on a spin column having a silica membrane and passed through the membrane using centrifugation for 1 min at about 6,000×g. The spin column is washed twice with a buffer containing ethanol and NaCl, the buffer being passed through the membrane, likewise using centrifugation for 1 min at about 6,000×g. The membrane is centrifuged to dryness for 3 min at 20,000×g, and the RNA is eluted with 50 μl of water free of RNase using centrifugation for 1 min at about 10,000×g.

During the procedure, all the fractions (supernatant, breakthrough, wash buffer, spin column, and eluate) are collected and thereafter, the distribution of the radiolabelled transcript in each fraction is determined by measurement in a scintillation counter.

TABLE 1

Distribution of radiolabelled RNA in supernatant and eluate as a function of amount of carrier. The difference to make 100% results from the amounts of RNA in the other fractions (spin column and wash buffer).

| Amount of carrier (μg) | RNA in supernatant (%) | RNA in eluate (%) |
|---|---|---|
| 0 | 83 | 3 |
| 2.5 | 79 | 13 |
| 5 | 63 | 26 |
| 7.5 | 49 | 39 |
| 10 | 30 | 55 |
| 25 | 5 | 75 |

Experiment B 2 ml of a 3.6% solution of tetradecyltrimethylammonium oxalate is added to 1 ml plasma in a 15 ml reaction vessel. Carrier RNA (poly A RNA having a length of 700 bases up to 7 kb) in varying amounts and radiolabelled transcript are placed in the cap of the reaction vessel. The cap of the reaction vessel is secured, the sample is mixed thoroughly and incubated for 10 min at room temperature. The complexes consisting of RNA and cationic compound are sedimented for 2 min at about 4,500×g.

Thereafter, the amount of radiolabelled transcript in sediment and supernatant is determined by measurement in a scintillation counter.

TABLE 2

Amount of radiolabelled RNA (%) in the sediment as a function of amount of carrier and centrifugation time. The difference to make 100% results from the amount of RNA in the supernatant.

| Centrifugation time (min) | 50 μg of carrier | 100 μg of carrier | 150 μg of carrier |
|---|---|---|---|
| 10 | 22% | nd | nd |
| 20 | 31% | 79% | 84% |
| 30 | 36% | nd | nd |
| 40 | 46% | 89% | 91% |

Both experiments show that very high amounts of carrier as well as high g values are necessary to pelletize the RNA/tetradecyltrimethylammonium oxalate complexes.

EXAMPLE 5

The advantages of the method according to the invention will be illustrated in the following Examples.

A radiolabelled in vitro transcript of the mouse Evx gene 4.5 kb in length was used as a model for the isolation of viral RNA from plasma. Radiolabelling was performed by incorporating $\alpha^{32}$P-UTP in the RNA transcript using T7 RNA polymerase.

1 ml of a 0.5% solution of ethanediyl-1,2-bis(dimethyldecylammonium bromide) is added to 1 ml plasma in a 15 ml reaction vessel. Carrier RNA (poly A RNA having a length of 700 bases up to 7 kb) in varying amounts and radiolabelled transcript are placed in the cap of the reaction vessel. The cap of the reaction vessel is secured, the sample is mixed thoroughly and incubated for 10 min at room temperature. The complexes consisting of RNA and cationic compound are sedimented for 20 min at about 4,500×g.

Thereafter, the amount of radiolabelled transcript in sediment and supernatant is determined by measurement in a scintillation counter.

TABLE 3

Amount of radiolabelled RNA (%) in the sediment as a function of amount of carrier and centrifugation time. The difference to make 100% results from the amount of RNA in the supernatant.

| Amount of carrier (µg) | RNA in sediment (%) |
|---|---|
| 0 | 95% |
| 5 | 96% |
| 10 | 94% |

Despite low amounts of carrier or even none at all, and despite sedimentation of the complexes consisting of RNA and cationic compounds at low g values, a high yield of RNA in the sediment is obtained.

EXAMPLE 6

Concentrating the Complexes Consisting of RNA and Cationic Compounds on Various Membranes 200 µl of plasma is mixed with 200 µl of a 1% solution of ethanediyl-1,2-bis(dimethyldecylammonium bromide). Radiolabelled transcript (see Example 5) is placed in the cap of the reaction vessel. No additional carrier RNA is added. The cap of the reaction vessel is secured, the sample is mixed thoroughly and incubated for 10 min at room temperature. The complexes consisting of RNA and cationic compound are concentrated on various membranes by passing them through these membranes using centrifugation for 2 min at 10,000×g in spin columns containing an appropriate membrane which is placed on a polypropylene frit for mechanical support and fixed with a lock ring. Here, soluble components do not bind to the membrane.

Thereafter, the amount of radiolabelled transcript in the breakthrough and on the spin column is determined by measurement in a scintillation counter.

TABLE 4

Amount of radiolabelled RNA (%) retained on each membrane. The difference to make 100% results from the amount of RNA in the breakthrough. Double determinations were conducted each time.

| Membrane | Yield |
|---|---|
| Pall Hydrolon HNPH 3R, pore size 3 µm | 21% |
| Nylon, hydrophobic | 20% |
| Pall Hydrolon HNPH 3R, pore size 1.2 µm | 39% |
| Nylon, hydrophobic | 38% |
| Pall (FluoRepel) Supor 450 | 43% |
| Polyethersulfone, hydrophobic | 46% |
| Pall Fluorotrans PVDF 0.2 µm | 40% |
| Poly(vinylidene difluoride), hydrophobic | 40% |

The result shows that the complexes of nucleic acid and cationic compound can be concentrated on suitable membranes as well.

EXAMPLE 7

Isolation of RNA from Plasma by Complexing with Cationic Compounds and Subsequent Purification on a Silica Membrane In a 2 ml reaction vessel, 1 ml of plasma is added with 1 ml of lysis buffer which, in addition to 1-20% (w/v) ethanediyl-1,2-bis(dimethyldecylammonium bromide), contains urea at a concentration of 1-6 M, and/or tributyl phosphate at a concentration of 0.1-1% (v/v), and/or dithiothreitol at a concentration of 5-40 mM, and/or isopropanol at a concentration of 10-50% (w/v). Radiolabelled transcript and 10 µg of poly A carrier RNA (see Example 4) are pipetted into the cap of the reaction vessel, the cap is secured, and the batch is mixed thoroughly. The batch is incubated for 10 min at room temperature. The complexes of RNA and cationic compound are sedimented in an Eppendorf 5417 centrifuge for 3 min at 3,000 rpm=about 1000×g, and the supernatant is pipetted off. The pellet is dissolved in 500 µl of a trishydroxymethylaminomethane (Tris HCl) buffer having a pH value of 6-8 and a high salt concentration, e.g. 2-5 M LiCl, 2-5 M sodium acetate, 4-6 M guanidinium thiocyanate or 2-6 M guanidine hydrochloride (GuHCl). For improved resuspending of the pellet, the buffer may be heated to 60° C. Furthermore, proteinase K (400 µg) may be added to the buffer, and the batch may then be incubated for 10 min at 60° C. Subsequently, 500 µl of a solution is added which contains 40-98% (v/v) ethanol. In addition, one or both of these solutions may contain a non-ionic or zwitterionic detergent such as Triton X-100, Nonidet-P40, TWEEN 20, CHAPSO, or ZWITTERGENT 3-12 at a concentration ranging from 1 to 20%. The solution is loaded on a spin column containing a silica membrane and passed through the membrane using centrifugation for 1 min at about 3,700×g. The spin column is washed twice with 700 µl of a buffer containing ethanol and NaCl, the wash buffer being passed through the membrane using centrifugation at 10,000×g. The spin column is centrifuged to dryness for 3 min at 20,000×g, and the RNA is eluted in two steps from the silica membrane using 30 µl of water each time.

During the procedure, all the fractions (supernatant, breakthrough, spin column, and eluate) are collected and thereafter, the distribution of radiolabelled transcript in each fraction is determined by measurement in a scintillation counter.

Table 5 exemplifies the results of purifications of radiolabelled RNA from plasma conducted under the conditions specified above.

TABLE 5

Yield of radiolabelled RNA in the eluate. The figures are in percent of the total amount of radioactive RNA employed. The difference to make 100% results from the amount of RNA in the other fractions (supernatant, breakthrough and spin column).

| Lysis buffer | Purification buffer | Yield |
|---|---|---|
| 1% Ethanediyl-1,2-bis(dimethyldecylammonium bromide), 50 mM Tris HCl pH 7.5 | 2 M GuHCl 50 mM Tris HCl pH 7.5<br>80% (v/v) ethanol | 42% |
| 1% Ethanediyl-1,2-bis(dimethyldecylammonium bromide), 50 mM Tris HCl pH 7.5 | 3 M GuHCl 50 mM Tris HCl pH 7.5<br>80% (v/v) ethanol | 45% |
| 1% Ethanediyl-1,2-bis(dimethyldecylammonium bromide), 50 mM Tris HCl pH 7.5 | 5 M GuHCl 50 mM Tris HCl pH 7.5<br>80% (v/v) ethanol | 53% |
| 1% Ethanediyl-1,2-bis(dimethyldecylammonium bromide), 50 mM Tris HCl pH 7.0 | 6 M GuHCl 50 mM Tris HCl pH 7.0<br>40% (v/v) ethanol | 40% |
| 1% Ethanediyl-1,2-bis(dimethyldecylammonium bromide), 50 mM Tris HCl pH 7.0 | 6 M GuHCl 50 mM Tris HCl pH 7.0<br>60% (v/v) ethanol | 32% |
| 1% Ethanediyl-1,2-bis(dimethyldecylammonium bromide), 50 mM Tris HCl pH 7.0 | 6 M GuHCl 50 mM Tris HCl pH 7.0<br>80% (v/v) ethanol | 24% |
| 1% Ethanediyl-1,2-bis(dimethyldecylammonium bromide), 50 mM Tris HCl pH 7.0 | 6 M GuHCl 50 mM Tris HCl pH 7.0<br>98% (v/v) ethanol | 31% |
| 20% Ethanediyl-1,2-bis(dimethyldecylammonium bromide), 50 mM Tris HCl pH 7.0, 3 M urea | 6 M GuHCl 50 mM Tris HCl pH 7.0<br>80% (v/v) ethanol, 10% (v/v) Nonidet P40 | 50% |
| 20% Ethanediyl-1,2-bis(dimethyldecylammonium bromide), 50 mM Tris HCl pH 7.0, 6 M urea | 6 M GuHCl 50 mM Tris HCl pH 7.0<br>80% (v/v) ethanol, 10% (v/v) Nonidet P40 | 32% |
| 5% Ethanediyl-1,2-bis(dimethyldecylammonium bromide), 50 mM Tris HCl pH 7.0, 3 M urea, 0.2% (v/v) tributyl phosphate | 6 M GuHCl 50 mM Tris HCl pH 7.0<br>80% (v/v) ethanol, 10% (v/v) Nonidet P40 | 64% |
| 5% Ethanediyl-1,2-bis(dimethyldecylammonium bromide), 50 mM Tris HCl pH 7.0, 3 M urea, 0.6% (v/v) tributyl phosphate | 6 M GuHCl 50 mM Tris HCl pH 7.0<br>80% (v/v) ethanol, 10% (v/v) Nonidet P40 | 50% |
| 5% Ethanediyl-1,2-bis(dimethyldecylammonium bromide), 50 mM Tris HCl pH 7.0, 3 M urea, 0.8% (v/v) tribbutyl phosphate | 6 M GuHCl 50 mM Tris HCl pH 7.0<br>80% (v/v) ethanol, 10% (v/v) Nonidet P40 | 36% |
| 1% Ethanediyl-1,2-bis(dimethyldecylammonium bromide), 50 mM Tris HCl pH 7.0, 3 M urea, 30% (v/v) isopropanol | 6 M GuHCl 50 mM Tris HCl pH 7.0<br>5% (v/v) Nonidet P40<br>80% (v/v) ethanol, 10% (v/v) Nonidet P40 | 66% |
| 1% Ethanediyl-1,2-bis(dimethyldecylammonium bromide), 50 mM Tris HCl pH 7.0, 3 M urea, 40% (v/v) isopropanol | 6 M GuHCl 50 mM Tris HCl pH 7.0<br>5% (v/v) Nonidet P40<br>80% (v/v) ethanol, 10% (v/v) Nonidet P40 | 49% |
| 2% Ethanediyl-1,2-bis(dimethyldecylammonium bromide), 50 mM Tris HCl pH 7.0, 3 M urea, 30% (v/v) isopropanol 10 mM Dithiothreitol | 6 M GuHCl 50 mM Tris HCl pH 7.0<br>5% (v/v) Nonidet P40<br>80% (v/v) ethanol, 10% (v/v) Nonidet P40 | 65% |
| 2% Ethanediyl-1,2-bis(dimethyldecylammonium bromide), 50 mM Tris HCl pH 7.0, 4 M urea, 30% (v/v) isopropanol 5 mM Dithiothreitol, 0.3% (v/v) tributyl phosphate | 6 M GuHCl 50 mM Tris HCl pH 7.0<br>5% (v/v) Nonidet P40<br>80% (v/v) ethanol, 10% (v/v) Nonidet P40 | 71% |
| 2% Ethanediyl-1,2-bis(dimethyldecylammonium bromide), 50 mM Tris HCl pH 7.0, 4 M urea, 30% (v/v) isopropanol 5 mM Dithiothreitol, 0.3% (v/v) tributyl phosphate | 6 M GuHCl 50 mM Tris HCl pH 7.0<br>1% (v/v) Nonidet P40, 400 μg proteinase K<br>80% (v/v) ethanol, 10% (v/v) Nonidet P40 | 78% |
| 1% Ethanediyl-1,2-bis(dimethyldecylammonium bromide), 50 mM Tris HCl pH 7.5 | 2 M LiCl 50 mM Tris HCl pH 7.5<br>80% (v/v) ethanol | 39% |
| 1% Ethanediyl-1,2-bis(dimethyldecylammonium bromide), 50 mM Tris HCl pH 7.5 | 5 M LiCl 50 mM Tris HCl pH 7.5<br>80% (v/v) ethanol | 38% |
| 2% Ethanediyl-1,2-bis(dimethyldecylammonium bromide), 50 mM Tris HCl pH 7.5 | 2 M sodium acetate pH 6.5<br>70% (v/v) ethanol | 31% |
| 2% Ethanediyl-1,2-bis(dimethyldecylammonium bromide), 50 mM Tris HCl pH 7.5 | 4 M sodium acetate pH 6.5<br>70% (v/v) ethanol | 30% |
| 1% Ethanediyl-1,2-bis(dimethyldecylammonium bromide), 50 mM Tris HCl pH 7.5 | 4 M guanidinium thiocyanate,<br>50 mM Tris HCl pH 7.0<br>80% (v/v) ethanol | 59% |
| 1% Ethanediyl-1,2-bis(dimethyldecylammonium bromide), 50 mM Tris HCl pH 7.5 | 6 M guanidinium thiocyanate,<br>50 mM Tris HCl pH 7.0<br>80% (v/v) ethanol | 46% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5,<br>1% (v/v) Triton X-100, 98% (v/v) ethanol | 34% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5,<br>5% (v/v) Triton X-100, 80% (v/v) ethanol | 43% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5,<br>1% (v/v) TWEEN 20, 80% (v/v) ethanol | 20% |
| 1% Ethanediyl-1.2-bis(dimethyldecylammonium bromide), 50 mM Tris HCl pH 7.5 | 5.5 M guanidinium thiocyanate, 40 mM sodium citrate pH 7.5,<br>3% (v/v) TWEEN 20, 98% (v/v) ethanol | 20% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5,<br>3% (w/v) ZWITTERGENT 3-12<br>98% (v/v) ethanol | 56% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5,<br>5% (w/v) ZWIITTERGENT 3-12<br>98% (v/v) ethanol | 37% |

TABLE 5-continued

Yield of radiolabelled RNA in the eluate. The figures are in percent of the total amount of radioactive RNA employed. The difference to make 100% results from the amount of RNA in the other fractions (supernatant, breakthrough and spin column).

| Lysis buffer | Purification buffer | Yield |
|---|---|---|
| 1% Ethanediyl-1,2-bis(dimethyldecylammonium bromide), 50 mM Tris HCl pH 7.5 | 5.5 M guanidinium thiocyanate, 40 mM sodium citrate pH 7.5, 1% (w/v) CHAPSO, 98% (w/v) ethanol | 22% |
| 1% Ethanediyl-1,2-bis(dimethyldecylammonium bromide), 50 mM Tris HCl pH 7.5 | 5.5 M guanidinium thiocyanate, 40 mM sodium citrate pH 7.5, 3% (w/v) CHAPSO, 98% (v/v) ethanol | 19% |

EXAMPLE 8

Isolation of Total RNA from HeLa Cells

A cell pellet consisting of $1 \times 10^7$ HeLa cells from a suspension culture is taken up in 1 ml of a 2% solution (w/v) of ethanediyl-1,2-bis(dimethyldecylammonium bromide) buffered with a Tris-HCl buffer pH 7.0 and added with 10 µl of β-mercaptoethanol per ml solution, reduced in size using a Polytron homogenizer in an Eppendorf reaction vessel, and incubated for 10 min at room temperature.

Thereafter, the solution is centrifuged for 3 min at about 1000×g. The supernatant is removed, and the sediment is dissolved in 200 µl of a solution consisting of 4 M guanidinium thiocyanate, 0.2 M sodium acetate and 10% (v/v) Nonidet P40. Thereafter, 100 µl of acidic phenol is added, and the solution is extracted by vigorous agitation. Following addition of 100 µl of chloroform, the solution is extracted once more by vigorous agitation and centrifuged for 1 min at 20,000×g to effect phase separation. The aqueous phase is removed and re-extracted with 100 µl of chloroform as described above. The aqueous phase is removed, and the nucleic acids are precipitated by adding 200 µl of isopropanol over 30 min at −20° C. The precipitated nucleic acids are sedimented by centrifuging for 5 min at 20,000×g, the supernatant is removed, and the nucleic acid sediment is washed once with an 80% ethanol solution, dried and dissolved in distilled water free of RNase.

The amount of isolated nucleic acid is determined by measuring the light absorption at a wavelength of 260 nm, and the purity of the nucleic acid is established by determining the ratio of light absorption at 260 nm and 280 nm (see Table 6).

TABLE 6

RNA yield and purity when using $1 \times 10^7$ HeLa cells. To determine the yield, the calculation factor for RNA is used (1 $OD_{260nm}$ = 40 µg/ml), the OD measurement is performed in water. A triple determination is carried out.

| Sample No. | Yield (µg) | OD 260 nm/280 nm |
|---|---|---|
| 1 | 51.2 | 1.85 |
| 2 | 135 | 1.66 |
| 3 | 77.9 | 1.69 |

The result conforms to the expected amount of total RNA that could be isolated from $10^7$ HeLa cells.

EXAMPLE 9

Isolation of Total RNA from Mouse Kidney

In 1 ml of a solution which contains 2% (w/v) ethanediyl-1,2-bis(dimethyldecylammonium bromide), 3 M urea and 10 µl β-mercaptoethanol per ml solution and is buffered with 50 mM Tris-HCl buffer pH 7.0, 20 mg of kidney tissue at a time is minced using a Polytron homogenizer in an Eppendorf reaction vessel and subsequently incubated for 10 min at room temperature. Thereafter, the solution is centrifuged for 3 min at about 1000×g.

The supernatant is removed, and the sediment is dissolved in 200 µl of a solution consisting of 4 M guanidinium thiocyanate, 0.2 M sodium acetate and 10% (v/v) Nonidet P40. Thereafter, 100 µl of acidic phenol is added, and the solution is extracted by vigorous agitation. Following addition of 100 µl of chloroform, the solution is extracted once more by vigorous agitation and centrifuged for 1 min at 20,000×g to effect phase separation. The aqueous phase is removed and re-extracted with 100 µl of chloroform as described above. The aqueous phase is removed, and the nucleic acids are precipitated by adding 200 µl of isopropanol over 30 min at −20° C. The precipitated nucleic acids are sedimented by centrifuging for 5 min at 20,000×g, the supernatant is removed, and the nucleic acid sediment is washed once with an 80% ethanol solution, dried and dissolved in distilled water free of RNase.

The amount of isolated nucleic acid is determined by measuring the light absorption at a wavelength of 260 nm, and the purity of the nucleic acid is established by determining the ratio of light absorption at 260 nm and 280 nm (see Table 7).

TABLE 7

RNA yield and purity when using 20 mg of kidney tissue. To determine the yield, the calculation factor for RNA is used (1 $OD_{260nm}$ = 40 µg/ml), the measurement is performed in water. A triple determination is carried out.

| Sample No. | Yield (µg) | OD 260 nm/280 nm |
|---|---|---|
| 1 | 220 | 1.31 |
| 2 | 207 | 1.90 |
| 3 | 256 | 2.26 |

EXAMPLE 10

Purification of RNA from Plasma by Complexing with Cationic Compounds and Subsequent Phenol/Chloroform Extraction As a model for viral RNA (e.g. HCV or HIV RNA), HeLa RNA is added to a mixture of 140 µl of blood plasma and 140 µl of a solution of 2% (w/v) ethanediyl-1,2-bis(dimethyldecylammonium bromide), buffered with 50 mM Tris-HCl pH 7.0, and subsequently incubated for 10 min. The solution then is centrifuged for 3 min at about 1000×g.

The supernatant is removed, and the sediment is dissolved in 200 µl of a solution consisting of 4 M guanidinium thiocyanate, 0.2 M sodium acetate and 10% (v/v) Nonidet P40. Thereafter, 100 µl of acidic phenol is added, and the solution is extracted by vigorous agitation. Following addition of 100 µl of chloroform, the solution is extracted once more by vigorous agitation and centrifuged for 1 min at 20,000×g to effect phase separation. The aqueous phase is removed and re-extracted with 100 µl of chloroform as described above. The aqueous phase is removed, and the nucleic acids are precipitated by adding 200 µl of isopropanol over 30 min at −20° C. The precipitated nucleic acids are sedimented by centrifuging for 5 min at 20,000×g, the supernatant is removed, and the nucleic acid sediment is washed once with an 80% ethanol solution, dried and dissolved in distilled water free of RNase.

The amount of isolated nucleic acid is determined by measuring the light absorption at a wavelength of 260 nm, and the purity of the nucleic acid is established by determining the ratio of light absorption at 260 nm and 280 nm (see Table 8).

TABLE 8

RNA yield and purity. To determine the yield, the calculation factor for RNA is used (1 $OD_{260nm}$ = 40 µg/ml), the measurement is performed in water. A triple determination is carried out.

| Sample No. | Yield (µg) | OD 260 nm/280 nm |
|---|---|---|
| 1 | 13.3 | 1.73 |
| 2 | 18.7 | 1.72 |
| 3 | 16.4 | 1.91 |

EXAMPLE 11

Isolation of RNA by complexing with cationic compounds and subsequent purification using membrane technologies described in patent application file No. PCT/EP98/06756.

10 µg of RNA at a time in 100 µl of water is added with 100 µl of a 2% ethanediyl-1,2-bis(dimethyldecylammonium bromide) solution in 50 mM Tris-HCl, pH 7.0, and incubated for 10 min in an Eppendorf reaction vessel at room temperature. Thereafter, the solution is centrifuged for 3 min at 20,000×g, the supernatant is decanted, and the pellet is dissolved in 300 µl of a solution of 6 M guanidine hydrochloride, 50 mM Tris-HCl, pH 7.0, and 1% (v/v) Nonidet P40. Following addition of 300 µl of a solution of 80% ethanol and 10% Nonidet P40 (v/v), the batches are passed through a membrane using centrifugation for one minute at 10,000×g in a plastic column containing a polypropylene frit for mechanical support on which a membrane for binding the nucleic acids is fixed by means of a lock ring.

1. Pall Fluoro Trans G, Poly(vinylidene difluoride), hydrophobic, pore size 0.2 µm,
2. GORE-TEX polyester fleece 9318, polytetrafluoroethylene, hydrophilic, pore size 3 µm,
3. Millipore Fluoropore PTFE, polytetrafluoroethylene, hydrophobic, pore size 3 µm, are used as membranes.

The material having passed through is collected in a collecting tube and discarded. The membranes are washed successively with 600 µl of a buffer containing guanidinium thiocyanate and with a buffer free of guanidinium thiocyanate where each of the wash buffers is passed through the membrane by centrifuging at 10,000×g. Subsequent to the second washing, the membranes are centrifuged to dryness for 2 min at 20,000×g. Thereafter, the RNA is eluted from the membrane by pipetting 70 µl of water onto the membrane and incubating for 2 min at room temperature. The eluate is pipetted from the top of the membrane using a pipette. The elution is repeated with another 70 µl of water, and the eluates are combined.

The amount of isolated RNA is determined by measuring the light absorption at a wavelength of 260 nm, and the purity of the RNA is established by determining the ratio of light absorption at 260 nm and 280 nm (see Table 9).

TABLE 9

RNA yield and purity. To determine the yield, the calculation factor for RNA is used (1 $OD_{260nm}$ = 40 µg/ml). The measurement is performed in water. Quadruple determinations are carried out each time.

| Membrane | Yield (µg) | OD 260 nm/280 nm |
|---|---|---|
| Pall Fluoro Trans G | 4.95 | 1.96 |
|  | 2.32 | 1.99 |
|  | 4.73 | 1.96 |
|  | 2.49 | 1.98 |
| GORE-TEX polyester fleece 9318 | 3.25 | 1.90 |
|  | 3.07 | 1.80 |
|  | 1.52 | 1.66 |
|  | 2.57 | 1.88 |
| Millipore Fluoropore PTFE | 4.32 | 1.99 |
|  | 7.08 | 1.99 |
|  | 7.66 | 1.97 |
|  | 7.25 | 1.98 |

EXAMPLE 12

Stabilization of RNA in Blood Using Cationic Compounds Having Two or More Ammonium Centers 200 µl of fresh blood at a time is added with 600 µl of a solution of:

2% (w/v) ethanediyl-1,2-bis(dimethyldecylammonium bromide) in 200 mM sodium citrate pH 3.0

2% (w/v) propanediyl-1,2-bis(dimethyldecylammonium bromide) in 200 mM sodium citrate pH 3.0

2% (w/v) ethanediyl-1,2-bis(dimethyltetradecylammonium bromide) in 200 mM sodium citrate pH 3.0

2% (w/v) N,N',N"-tridecyl-N,N,N',N",N"-pentamethyl-bis (2-ammonioethyl)ammonium bromide in 200 mM sodium citrate pH 3.0 and stored for 48 hours at room temperature. All of the batches were conducted as double determinations.

To isolate the RNA, the samples are centrifuged for 2 min at 1,000×g, the supernatant is decanted, and the pellet is dissolved in 700 µl of a solution of 6 M guanidine hydrochloride, 200 mM Tris-HCl, pH 7.0, and 1% (v/v) Nonidet P40. Thereafter, 80 µg of proteinase K is added, and the batches are incubated for 30 min at 40° C. 350 µl of acidic phenol is added each time, and the batches are extracted by vigorous agitation. Following addition of 350 µl of chloro-form and another extraction, the batches are centrifuged for 3 min at 14,000×g to effect phase separation. The aqueous phase is removed and extracted once more with 700 µl of chloroform. Following another centrifugation, the aqueous phase is removed again, and the RNA is precipitated by adding 70 µl of 3 M sodium acetate, pH 5.2, and 700 µl of isopropanol over 30 min at −20° C. The RNA is centrifuged off over 10 min at 20,000×g, the supernatant is removed, the pellet is washed once with 600 ml of 80% (v/v) ethanol, subsequently dried and redissolved in 100 µl of water free of RNase.

The amount of isolated RNA is determined by measuring the light absorption at a wavelength of 260 nm, and the purity of the RNA is established by determining the ratio of light absorption at 260 nm and 280 nm (see Table 10).

TABLE 10

RNA yield and purity. To determine the yield, the calculation factor for RNA is used (1 $OD_{260nm}$ = 40 µg/ml). Double determinations are carried out each time.

| Cationic compound | Yield (µg) | OD 260 nm/ 280 nm |
|---|---|---|
| Ethanediyl-1,2-bis(dimethyldecyl- ammonium bromide) | 0.36 | 1.24 |
| | 0.60 | 1.14 |
| Propanediyl-1,2-bis(dimethyldecyl- ammonium bromide) | 3.2 | 1.01 |
| | 0.72 | 1.1 |
| Ethanediyl-1,2-bis(dimethyltetradecyl- ammonium bromide) | 0.96 | 1.15 |
| | 1.2 | 1.05 |
| N,N',N''-tridecyl-N,N,N',N'',N''-pentamethyl- bis(2-ammonioethyl)ammonium bromide | 0.72 | 1.17 |
| | 1.8 | 0.72 |

EXAMPLE 13

Isolation of RNA Using Cationic Substances Having Two or More Ammonium Centers

25 µg of pure HeLa RNA at a time, dissolved in 140 µl of water, is added with 140 µl of the substances dissolved in water at varying concentrations of 1-15% (w/v) and incubated at RT for 10 min, the substance-RNA complexes are centrifuged off over 10 min at 5,000×g, taken up in 150 µl of a buffer consisting of 3.5 M guanidinium thiocyanate, 25 mM sodium citrate, pH 7.5, and purified according to the following protocol. The sample is added with 150 µl of 70% ethanol. Using vacuum, the sample then is applied on a spin column containing a silica membrane. The spin column is washed twice with a wash buffer containing ethanol and NaCl, the wash buffer likewise being passed through the membrane by means of vacuum. The spin column is dried for 10 min using vacuum. Thereafter, the RNA is eluted twice using 60 µl of water each time, the spin column being centrifuged for 1 min at 10,000× g. The results are summarized in Table 11.

TABLE 11

Yield of HeLa RNA in the eluate as a function of the concentration of substance employed. To determine the yield, the calculation factor for RNA is used (1 $OD_{260nm}$ = 40 µg/ml).

| Substance | Concentration in % (w/v) | Yield (µg) |
|---|---|---|
| Ethanediyl-1,2-bis(dimethyldecylammonium bromide) | 1 | 22.2 |
| | 9 | 25.0 |
| | 15 | 19.5 |
| Ethanediyl-1,2-bis(dimethyldecylammonium thiosulfate) | 1 | 24.5 |
| | 9 | 25 |
| | 15 | 24 |
| Ethanediyl-1,2-bis(dimethyldecylammonium sulfate) | 1 | 22.2 |
| | 9 | 25 |
| | 15 | 22.4 |
| Ethanediyt-1,2-bis(dimethyldecylammonium iodide) | 1 | 18.9 |
| | 9 | 23 |
| | 15 | 19.2 |
| N,N',N''-tridecyl-N,N,N',N'',N''-pentamethyl-bis- (2-ammonio-ethyl)ammonium bromide | 1 | 15.3 |
| | 9 | 12.7 |
| | 13 | 23.2 |
| N,N',N''-tritetradecyl-N,N,N',N'',N''-pentamethyl- bis-2-ammonioethyl)ammonium bromide | 1 | 11.3 |
| | 9 | 9.9 |
| | 15 | 6.3 |
| Ethanediyl-1,2-bis(dimethyloctylammonium bromide) | 3 | 7.6 |
| | 15 | 6.5 |
| Propanediyl-1,2-bis(dimethyldecylammonium bromide) | 3 | 21.2 |
| | 8 | 24.6 |
| | 15 | 24.7 |
| Butanediyl-1,2-bis(dimethyldecylammonium bromide) | 1 | 24.6 |
| | 9 | 25 |
| | 13 | 11.3 |
| Ethanediyi-1,2-bis(dimethyldodecylammonium bromide) | 1 | 14.4 |
| | 8 | 14.5 |
| | 15 | 7.3 |
| Propanediyl-1,2-bis (dimethyltetradecylammonium bromide) | 1 | 13.8 |
| | 9 | 18 |
| | 15 | 14.6 |
| Hexadimethrine bromide | 1 | 9.6 |
| | 5 | 3 |

The results show that all of these substances can be used in complexing RNA. Under the selected conditions, however, some of these substances work significantly more effective compared to others.

EXAMPLE 14

Stabilization of RNA in Blood Using Cationic Compounds 1 ml of stabilization buffer, consisting of 2% (w/v) ethanediyl-1,2-bis(dimethyldecylammonium bromide), 50 mM potassium acetate, pH 5.5, and 50 mM Tris-HCl, pH 7.0, is added to 1 ml of blood. The batch is mixed thoroughly and stored for 24 hours or 96 hours at room temperature or 40° C. The complexes consisting of nucleic acid and cationic compound are centrifuged for 3 min at 4,000×g, the supernatant is removed, and the pellet is redissolved in 1 ml of a buffer consisting of 6 M guanidine hydrochloride, 50 mM Tris-HCl, pH 7.0, and 1% (v/v) Nonidet P40. Then, 800 µg of proteinase K is added, and the batch is incubated for 1 hour at 60° C. Thereafter, 1 ml of 80% (v/v) ethanol, 10% (v/v) Nonidet P40 are added, and using vacuum, the sample is applied on a spin column containing a silica membrane. The spin column is washed with 350 µl of a buffer containing guanidinium thiocyanate and ethanol. Then, 80 µl of Tris-HCl buffer containing $MgCl_2$ and 75 U of DNase I (Pharmacia) is pipetted on the silica membrane and incubated for 15 min at room temperature to degrade the genomic DNA. The spin column is washed once more with 350 µl of said buffer containing guanidinium thiocyanate and ethanol, and subsequently with 700 µl of a wash buffer containing ethanol. The spin column is centrifuged to dryness for 3 min at 20,000×g, and the RNA is eluted in two steps using 30 µl of water each time.

3 µl of this eluate at a time is employed for an RT PCR detection of β-actin mRNA in an ABI PRISM 7700 Sequence Detector (Applied Biosystems) (so-called TaqMan technology). The TaqMan technology uses oligonucleotide probes containing a reporter dye and a quencher dye. During PCR amplification, the 5'-3' exonuclease activity of Taq polymerase is utilized to separate the reporter dye from the quencher dye, thereby generating a sequence-specific fluorescence signal which increases with every amplification cycle. The quantification is based on the threshold cycle wherein a previously defined fluorescence limit is reached. A comparison of the threshold cycles provides a measure for the relative concentration of template in different samples. Measurement during the logarithmic phase, where PCR precision is a maximum, provides precise data for an accurate determination.

The results are illustrated in Table 12.

TABLE 12

Analysis of β-actin mRNA using the TaqMan ™ RT PCR.
The threshold cycles ($C_T$) of the TaqMan ™ evaluation are illustrated as a function of storage of the stabilized sample.
Each sample was subjected to a double determination in the ABI PRISM 7700 Sequence Detector.

| Storage | $C_T$ |
|---|---|
| 24 hours 4° C. | 17.23 |
|  | 18.51 |
| 96 hours 4° C. | 18.30 |
|  | 18.29 |
| 24 hours room temperature | 17.93 |
|  | 17.89 |
| 96 hours room temperature | 19.34 |
|  | 19.35 |

EXAMPLE 15

Stabilization of RNA in Plasma Using Cationic Compounds

In a 2 ml reaction vessel, 500 µl of plasma is added with 500 µl of a solution consisting of 2% (w/v) ethanediyl-1,2-bis(dimethyldecylammonium bromide), 200 mM sodium citrate, pH 3.0. 15 µg of HeLa RNA is pipetted into the cap of the reaction vessel, the cap is closed and the batch is mixed. One sample at a time is incubated for 10 min at room temperature and immediately thereafter subjected to further processing. The other samples are stored for 24 and 48 hours at 4° C., whereafter the RNA is isolated. As a control, the HeLa RNA is pipetted directly into the plasma, and after 10 seconds, 500 µl of 2% (w/v) ethanediyl-1,2-bis(dimethyl-decylammonium bromide), 200 mM sodium citrate, pH 3.0, are added and incubated for another 10 min at room temperature before the sample preparation is carried out, or, the controls are stored together with the stabilized samples for 24 and 48 hours at 4° C. For sample preparation, 500 µl of 2% (w/v) ethanediyl-1,2-bis(dimethyldecylammonium bromide), 200 mM sodium citrate, pH 3.0, then are added, the batch is incubated for 10 min at room temperature and then processed further.

The complexes consisting of RNA and cationic compound are centrifuged for 3 min at about 1,100×g, the supernatant is removed, and the pellet is redissolved in 600 µl of a buffer consisting of 6 M guanidine hydrochloride, 50 mM Tris-HCl, pH 7.0, and 1% (v/v) Nonidet P40. Then, 800 µg of proteinase K is added, and the batch is incubated for 30 min at 40° C. Thereafter, 600 µl of 80% (v/v) ethanol, 10% (v/v) Nonidet P40 are added, and the sample is applied on a spin column containing a silica membrane, the sample being passed through the membrane using centrifugation at 3,700×g for 1 min.

The spin column is washed with 350 µl of a buffer containing guanidinium thiocyanate and ethanol. Then, 80 µl of Tris-HCl buffer containing MgCl$_2$ and 75 U of DNase I (Pharmacia) is pipetted on the silica membrane and incubated for 15 min at room temperature to degrade the genomic DNA. The spin column is washed once more with 350 µl of said buffer containing guanidinium thiocyanate and ethanol, and subsequently with 500 µl at a time of a wash buffer containing ethanol. The spin column is centrifuged to dryness for 3 min at 20,000×g, and the RNA is eluted in two steps using 50 µl of water each time. 4 µl of this eluate at a time is employed in an RT PCR detection of β-actin mRNA in an ABI PRISM 7700 Sequence Detector (Applied Biosystems). The reaction conditions for the RT PCR detection are identical to those described in Example 12. 30 µl of the eluate at a time is separated in a 1.2% agarose/formaldehyde/MOPS gel. The results are illustrated in Table 13 and FIG. 1.

TABLE 13

Analysis of β-actin mRNA using the TaqMan ™ RT PCR.
The threshold cycles ($C_T$) of the TaqMan ™ evaluation are illustrated as a function of storage time of the stabilized samples and the controls. Each sample was subjected to a double determination in the ABI PRISM 7700 Sequence Detector.

| Storage | Stabilized sample | Control |
|---|---|---|
| 10 min RT* | 15.90 | 21.49 |
|  | 16.17 | 22.16 |
| 24 hours 4° C. | 16.25 | 40** |
|  | 15.82 | 40** |
| 48 hours 4° C. | 16.43 | 40** |
|  | 16.49 | 40** |

*In the control, the RNA is incubated for about 10 seconds in the plasma in an unprotected state before the stabilization buffer is added and incubation is continued for another 10 min at room temperature.
**Within these 40 cycles, there is no amplification of β-actin mRNA.

In the Examples 14 and 15, the mRNA of the β-actin gene was detected using amplification in an ABI PRISM 7700 Sequence Detector.

The β-actin mRNA was amplified in a one-pot TaqMan RT PCR. For a 25 µl reaction batch, standard reagents in the form of a kit from Perkin Elmer Applied Biosystems Company (TaqMan PCR Reagent Kit, β-Actin Detection Kit, AmpliTaq Gold DNA polymerase, MuLV reverse transcriptase) and from Promega Company (RNasin) were used. The cDNA was synthesized over 60 min at 37° C., and the AmpliTaq Gold DNA polymerase was subsequently activated for 12 min at 95° C. The specific β-actin fragment was amplified in a directly following PCR. To this end, 40 PCR cycles were performed with 15 seconds at 95° C. and 1 minute at 60° C.

In Example 15, the increase of the $C_T$ value (threshold cycle value) from about 16 to about 22 in the control sample "10 min RT", to which the stabilization buffer has been added only after 10 seconds, indicates that more than 99% of the RNA has been degraded (Control 10 min RT) within those 10 seconds where the RNA has been present in the plasma in an unprotected state. Here, a difference of 1 threshold cycle (1 $C_T$) has been assumed to indicate an approximately twofold difference of the amounts of β-actin mRNA in the samples to be analyzed. This result is confirmed by gel analysis wherein the control exhibits no more than a faint streak of highly degraded RNA (FIG. 1, lanes 4 and 5, 10 min room temperature). After a prolonged storage of 24 hours and 48 hours with no stabilization buffer added, the RNA in the controls is completely degraded (Control 24 hours 4° C. and Control 48 hours 4° C.). RNA is no longer detectable, neither in an agarose/formaldehyde gel electrophoresis (FIG. 1, lanes 4 and 5), nor in a β-actin TaqMan RT PCR (Controls) where a threshold of 40 indicates that no amplification signal has been generated during 40 PCR cycles and thus, no β-actin mRNA has been detectable.

In contrast, both the results of β-actin mRNA amplification and the results of gel analysis (FIG. 1) indicate that no degradation of RNA has occurred in the stored samples added with stabilization buffer (stabilized samples 10 min RT, 24 hours 4° C., 48 hours 4° C.). This can be seen in the clearly visible bands of ribosomal RNA in the gel and in the TaqMan RT PCR $C_T$ values which, considering the accuracy limits of this method, must be referred to as constant.

This result is also confirmed in Example 14 wherein a highly sensitive detection of β-actin mRNA in the blood sample by means of TaqMan™ RT PCR is possible even after storage for 96 hours at room temperature.

It has been demonstrated both for plasma and blood that it is possible to protect RNA in these biological samples from degradation by using cationic compounds. In contrast, unprotected RNA is completely degraded within a few seconds in both sample materials.

EXAMPLE 16

Isolation of Hela-RNA from Plasma, Using Ethanediyl-1,2-bis(dimethyldecylammonium bromide), buffered with Citric Acid in a pH Range from 3-7

15 µg of HeLa-RNA was spiked into 500 µl plasma and mixed with 500 µl of a buffer, containing 2% (w/v) Ethanediyl-1,2-bis(dimethyldecylammonium bromide) and 0.5 M citric acid of different pH-values (range from pH 3 to 7) and thereafter incubated for 10 minutes at room temperature. For the RNA isolation, the complexes consisting of the cationic substance and the nucleic acids, were pelleted by centrifugation at 1100×g for 3 minutes and the pellet was subsequently solved in 600 µl of a buffer containing 6 M guanidine hydrochloride, 1% (v/v) Nonidet-P40 and 50 mM Tris HCl pH 7.0. 800 µg Proteinase K was added and the sample incubated at 40° C. for 30 minutes. Then 600 µl of a solution, containing 80% (v/v) ethanol and 10% (v/v) Nonidet-P40 was added and the sample was applied to a spin column containing a silica membrane. The isolated RNA on the membrane was washed once with a buffer containing guanidine thiocyanate and ethanol and once with a buffer containing sodium chloride and ethanol. The silica membrane was dried by centrifugation of the spin column at 20 000×g for 3 minutes. The RNA was eluted form the silica membrane with 100 µl of RNAse free water by means of centrifugation. 30 µl of the eluate was applied to a 1.2% (w/v) agarose/formaldehyde gel.

As a negative control experiment (K), the HeLa-RNA was spiked directly into 500 µl of plasma and after ten seconds, 500 µl of a buffer, containing 2% (w/v) Ethanediyl-1,2-bis (dimethyldecylammonium bromide) and 0.5 M citric acid pH 3.0 was added. The sample was incubated additional 10 minutes and the RNA was isolated as described above.

Figure 2:
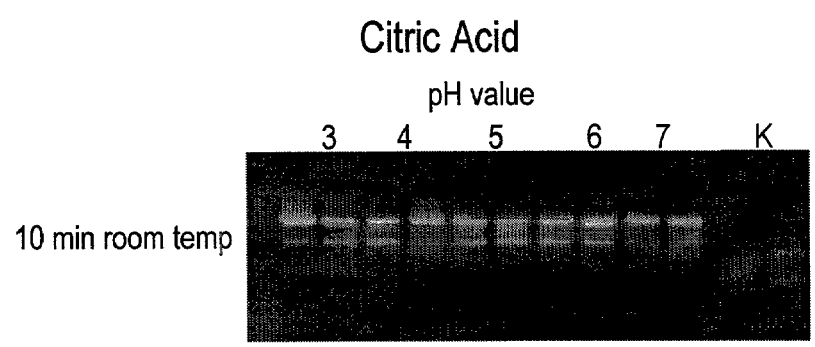

In FIG. 2 an agarose/formaldehyde gel picture shows the isolated RNA bands at different pH-values, whereas the samples were incubated 10 minutes at room temperature.

The experiment shows that within the entire pH range intact RNA can be isolated with the same efficiency. The negative control experiment (K), on the other hand, shows that unprotected RNA is degraded within seconds in plasma.

FIG. 17: Stabilization of HeLa-RNA from plasma, using Ethanediyl-1,2-bis(dimethyldecylammonium bromide), buffered with citric acid in a pH range from 3-5

15 µg of HeLa-RNA was spiked into 500 µl plasma mixed with 500 µl of a buffer, containing 2% (w/v) Ethanediyl-1,2-bis(dimethyldecylammonium bromide) and 0.5 M citric acid of different pH-values (range from pH 3 to 5) and incubated for 10 minutes at room temperature for 24 and 48 h at 4° C., respectively. For the isolation of the RNA, the complexes consisting of the cationic substance and the nucleic acids were pelleted by centrifugation at 1100×g for 3 minutes and the pellet was subsequently resolved in 600 µl of a buffer containing 6 M guanidine hydrochloride, 1% (v/v) Nonidet-P40 and 50 mM Tris HCl pH 7.0. 800 µg Proteinase K were added and the sample was incubated at 40° C. for 30 minutes. Then 600 µl of a solution, containing 80% (v/v) ethanol and 10% (v/v) Nonidet-P40 was added and the sample was applied to spin column containing silica membrane via centrifugation. The membrane was washed once with a buffer containing guanidine thiocyanate and ethanol and once with a buffer containing sodium chloride and ethanol. The silica membrane was dried by centrifugation at 20 000×g for 3 minutes. RNA was eluted form the silica membrane with 100 µl of RNAse free water by centrifugation. 30 µl of the respective eluate were applied on a 1.2% (w/v) agarose/formaldehyde gel.

As a negative control experiment (K), the HeLa-RNA was spiked directly into 500 µl of plasma and after ten seconds, 500 µl of a buffer, containing 2% (w/v) Ethanediyl-1,2-bis (dimethyldecylammonium bromide) and 0.5 M citric acid pH 3.0 was added. The sample was incubated additional 10 minutes and the RNA was isolated as described above.

Figure 3:
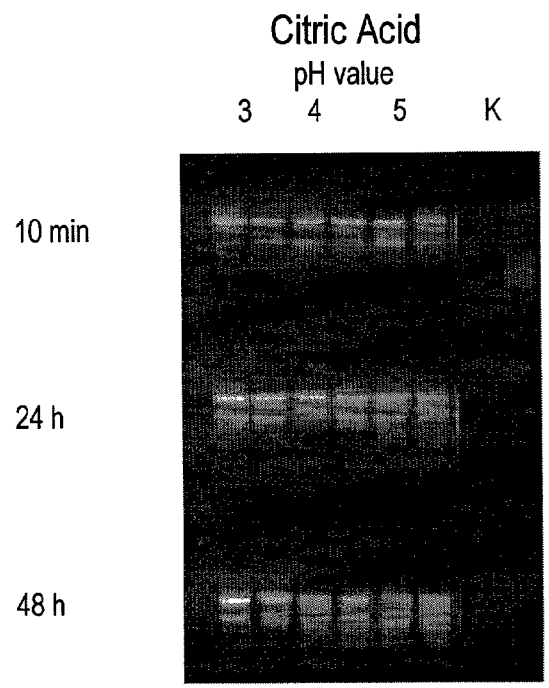

In FIG. 3 an agarose/formaldehyde gel picture shows the isolated RNA bands at different pH-values, whereas the samples were incubated 10 minutes at room temperature, 24 and 48 hours at 4° C.

The experiment shows, that RNA can be stabilized in plasma for a longer period of time with a buffer containing Ethanediyl-1,2-bis(dimethyldecylammonium bromide) and citric acid.

EXAMPLE 18

Isolation of Hela-RNA from Plasma, Using Cationic substances with two nitrogen- or phosphor centers, Linked by a Bridge Consisting of an Aromatic Compound or Ethane 5 µg of HeLa-RNA was spiked into 500 µl plasma and mixed with 500 µl of a solution containing one of the cationic substances A, B, C, D or E (see below) and incubated for 10 minutes at room temperature. For the isolation of the RNA, the complexes consisting of one of the cationic substance and the nucleic acids were pelleted by centrifugation at 1530×g for 3 minutes and the pellet was subsequently solved in 300 µl of a buffer containing 6 M guanidine hydrochloride, 1% (v/v) Nonidet-P40 and 50 mM Tris HCl pH 7.0. 400 µg Proteinase K was added and the sample was incubated at 40° C. for 10 minutes. Then 300 μl of a solution, containing 80% (v/v) ethanol and 10% (v/v) Nonidet-P40 was added and the sample was applied via centrifugation to a a silica membrane located in a spin column. The membrane was washed once with a buffer containing guanidine thiocyanate and ethanol and once with a buffer containing sodium chloride and ethanol. The silica membrane was dried by centrifugation at 20 000×g for 3 minutes. The RNA was eluted form the silica membrane with 80 μl of RNAse free water by centrifugation. 25 μl of the respective eluate was applied on a 1.2% (w/v) agarose/formaldehyde gel.

Figure 4:
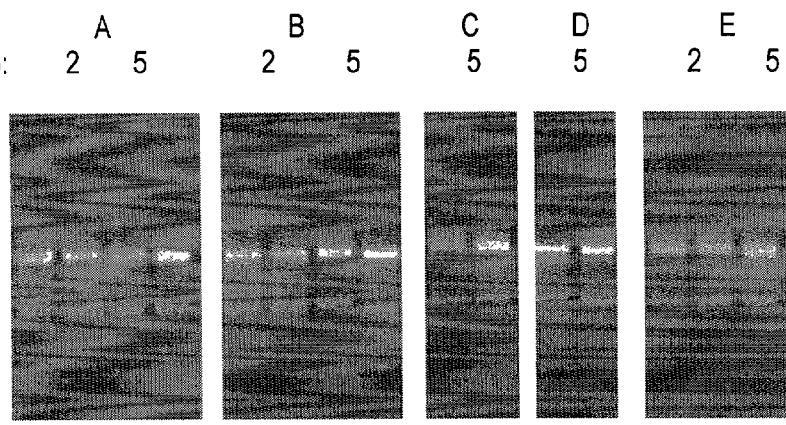

In FIG. 4 a plurality of five agarose/formaldehyde gel pictures show the isolated RNA bands for the five cationic substances A, B, C, D and E used:

A: o-Xylylene-bis-decyldimethylammonium bromide
B: m-Xylylene-bis-decyldimethylammonium bromide
C: p-Xylylene-bis-decyldimethylammonium bromide
D: [1,8]-dimethylnaphthaleno,alpha,alpha'-bis-dimethyldecylammonium bromide
E: Ethanediyl-1,2-bis(decyldimethylphosphonium bromide)

The experiment shows, that the cationic substances can be used to isolate RNA from plasma. The yields of the spiked RNA were between 63% (=3.2 μg) and 74% (=3.7 μg).

EXAMPLE 19

Isolation of RNA and Genomic DNA from $1 \times 10^6$ HeLa Cells, Using Cationic Substances with Two Nitrogen- or Phosphor Centers, Linked by a Bridge Consisting of an Aromatic Compound or Ethane $1 \times 10^6$ HeLa cells were dissolved in 500 μl PBS buffer and mixed with 500 μl of a solution of the cationic substance A, B, C, D or E (see below) and incubated for 10 minutes at room temperature. For the isolation of the RNA, the complexes consisting of the cationic substance and the nucleic acids were pelleted by centrifugation at 1530×g for 3 minutes and the pellet was subsequently resolved in 300 μl of a buffer containing 6 M guanidine hydrochloride, 1% (v/v) Nonidet-P40 and 50 mM Tris HCl pH 7.0. 400 μg Proteinase K were added and the sample was incubated at 40° C. for 10 minutes. Then 300 μl of a solution, containing 80% (v/v) ethanol and 10% (v/v) Nonidet-P40 was added and the sample was applied to a spin column containing silica membrane via centrifugation. The spin column was washed once with a buffer containing guanidine thiocyanate and ethanol and once with a buffer containing sodium chloride and ethanol. The silica membrane was dried by centrifugation at 20 000×g for 3 minutes. The RNA was eluted from the silica membrane with 80 μl of RNAse free water by centrifugation. 25 μl of the respective eluate was applied on a 1.2% (w/v) agarose/formaldehyde gel.

Figure 5:
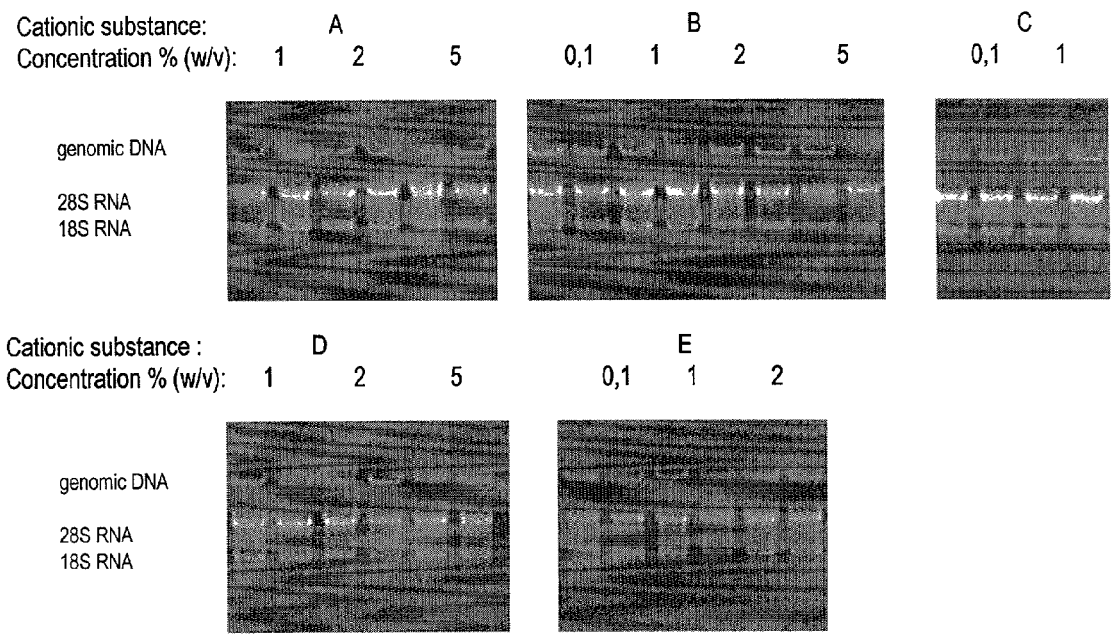

In FIG. 5 a plurality of five agarose/formaldehyde gel pictures show the isolated RNA and genomic DNA bands for the five cationic substances A, B, C, D and E used: *

A: o-Xylylene-bis-decyldimethylammonium bromide
B: m-Xylylene-bis-decyldimethylammonium bromide
C: p-Xylylene-bis-decyldimethylammonium bromide
D: [1,8]-dimethylnaphthaleno,alpha,alpha'-bis-dimethyldecylammonium bromide
E: Ethanediyl-1,2-bis(decyldimethylphosphonium bromide)

EXAMPLE 20

Isolation of Genomic DNA from Blood, Using Cationic Substances with Two Nitrogen- or Phosphor Centers, Linked by a Bridge Consisting of an Aromatic Compound or Ethane 0.5 ml of blood was mixed with 0.5 ml of a solution of the cationic substance A, B, C, D or E (see below) and incubated for 10 minutes at room temperature. For the isolation of the genomic DNA, the complexes consisting of the cationic substance and the nucleic acids were initially pelleted by centrifugation at 1530×g for 3 minutes and the pellet was subsequently resolved in 360 μl of a buffer containing EDTA and sodium chloride. Then, 400 μl of buffer AL (QIAGEN GmbH; Cat. No.: 19075) and 20 μl Proteinase K (18 mg/ml) were added and the sample was incubated at 65° C. for 10 minutes. Then 420 μl of ethanol was added and the sample was applied to a spin column containing silica membrane via centrifugation. The spin column was washed once with buffer AW 1 (QIAGEN GmbH, Cat. No.: 19081) and once with a buffer AW 2 (QIAGEN GmbH, Cat. No.: 19072). The silica membrane was dried by centrifugation at 20 000×g for 3 minutes. The DNA was eluted form the silica membrane with 100 μl of water by centrifugation. 25 μl of the eluate were analysed on a 0.8% (w/v) agarose/TBE gel.

Figure 6:
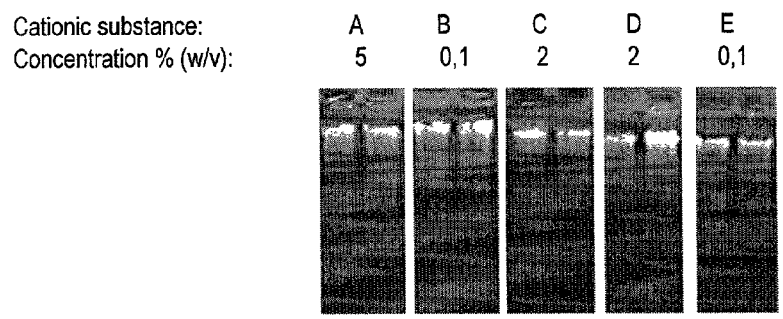

In FIG. 6 a plurality of five agarose/formaldehyde gel pictures show the genomic DNA bands for the five cationic substances A, B, C, D and E used: *

A: o-Xylylene-bis-decyldimethylammonium bromide
B: m-Xylylene-bis-decyldimethylammonium bromide
C: p-Xylylene-bis-decyldimethylammonium bromide
D: [1,8]-dimethylnaphthaleno,alpha,alpha'-bis-dimethyldecylammonium bromide
E: Ethanediyl-1,2-bis(decyldimethylphosphonium bromide)

The yields of genomic DNA from 0.5 ml of blood are in the range of 6 μg to 11 μg

EXAMPLE 21

Stabilization of RNA in Plasma, Using Cationic substances with two nitrogen- or phosphor centers, Linked by a Bridge Consisting of an Aromatic Compound or Ethane, Buffered with Tartaric Acid 6 μg of HeLa-RNA was spiked into 500 μl plasma mixed with 500 μl of a buffer, containing the cationic substance A, B, D or E (see below) in a concentration of 4 to 5% (w/v) and 0.25 M tartaric pH 4 and stored for 24 h at room temperature. For the RNA isolation, the complexes consisting of the cationic substance and the nucleic acids were initially pelleted by centrifugation at 1530×g for 3 minutes and the pellet was subsequently resolved in 300 μl of a buffer containing 6 M guanidine hydrochloride, 1% (v/v) Nonidet-P40 and 50 mM Tris HCl pH 7.0. 400 μg Proteinase K were added and the sample was incubated at 40° C. for 10 minutes. Then 300 μl of a solution, containing 80% (v/v) ethanol and 10% (v/v) Nonidet-P40, was added and the sample was applied to a spin column containing silica membrane via centrifugation. The spin column was washed once with a buffer containing guanidine thiocyanate and ethanol and once with a buffer containing sodium chloride and ethanol. The silica membrane was dried by centrifugation at 20 000×g for 3 minutes. The RNA was eluted form the silica membrane with 80 µl of RNAse free water by centrifugation. 25 µl of the eluate were analysed on a 1.2% (w/v) agarose/formaldehyde gel.

As a negative control reaction (K), the HeLa-RNA was spiked directly into 500 µl of plasma and after ten seconds, 500 µl of a buffer, containing 2% (w/v) Ethanediyl-1,2-bis(dimethyldecylammonium bromide) and 0.25 M tartaric acid pH 4.0 was added. The sample was incubated additional 10 minutes and the RNA was isolated as described above.

Figure 7:
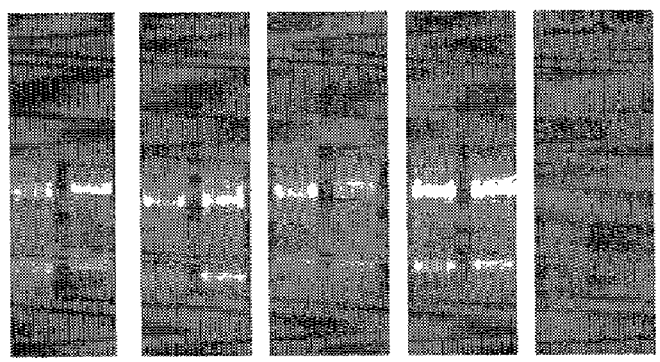

In FIG. 7 a plurality of five agarose/formaldehyde gel pictures show the isolated RNA bands for the four cationic substances A, B, D and E used, K shows the result of the negative control experiment: *
A: o-Xylylene-bis-decyldimethylammonium bromide
B: m-Xylylene-bis-decyldimethylammonium bromide
D: [1,8]-dimethylnaphthaleno,alpha,alpha'-bis-dimethyldecylammonium bromide
E: Ethanediyl-1,2-bis(decyldimethylphosphonium bromide)
K: negative control experiment

The invention claimed is:

1. A method of stabilizing unpurified nucleic acids in a biological sample from degradation comprising:
contacting a biological sample containing unpurified nucleic acid with at least one cationic compound of formula (I)

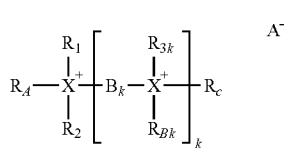

wherein (A) is an anion, and said anion is a conjugated base of a strong or weak inorganic or organic acid, or combinations thereof, and wherein the cationic compound (I) and anion (A), together, have a neutral charge,
and wherein
X is nitrogen (N),
k is the integer 1, 2, 3, or 4,
B represents a substituted or non-substituted aliphatic alkanediyl bridge, wherein the substituted aliphatic alkanediyl bridge is substituted on one or more carbon atoms, wherein one or more non-adjacent carbon atoms is replaced by oxygen, and wherein the substituted aliphatic alkanediyl bridge is the structure $(CH_2)_n$—$(OCH_2)_m$— wherein n and m independently represent the integer 0, 1, 2, 3, 4, 5, or 6, with n+m>0;
$R_1$, $R_2$ and $R_{3k}$, are independently selected from the group consisting of
methyl, ethyl, propyl, isopropyl, butyl, isobutyl, n-pentyl, isopentyl, and hexyl
$R_A$, $R_{Bk}$, $R_C$, are independently selected from the group consisting of an unsubstituted linear or branched $C_1$-$C_{21}$ alkyl, an unsubstituted linear or branched $C_1$-$C_{21}$ alkenyl, an unsubstituted linear or branched $C_1$-$C_{21}$ alkynyl,
and a structure $CH_3$—$(CH_2)_n$—Z—$(CH_2)_m$— wherein n, m are independent of each other, and n represents the integer 2, 3 or 4, m represents the integer 8, 9, 10, 11, 12, 13, 14, 15, 16, 17, or 18, and Z represents —O—, —CO—, —OCO—, —CO—N—, or —N—CO—;
wherein the unpurified nucleic acid in the biological sample forms a complex with the cationic compound (1) and is stabilized from degradation within said biological sample;
optionally concentrating the complexes of nucleic acid and cationic compound;
storing the complex of nucleic acid and cationic compound until further tests are conducted or a further purification is performed; and
optionally, isolating the stabilized nucleic acid from the biological sample.

2. A method of stabilizing unpurified nucleic acids in a biological sample from degradation comprising:
contacting a biological sample containing unpurified nucleic acid with at least one cationic compound, wherein the cationic compound has the formula:

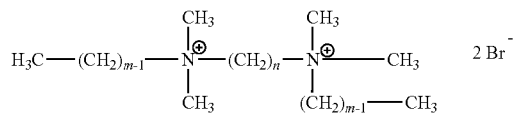

wherein n is 1, 2, 3, or 4 and m is an integer between 8 and 20, inclusive.

3. The method according to claim 2, wherein said cationic compound is selected from the group consisting of ethanediyl-1,2-bis(dimethyldecylammonium bromide); propanediyl-1,2-bis(dimethyldecylammonium bromide); and ethanediyl-1,2-bis(dimethyltetradecylammonium bromide).

4. A method of stabilizing unpurified nucleic acids in a biological sample from degradation comprising:
contacting a biological sample containing unpurified nucleic acid with at least one cationic compound of formula (I)

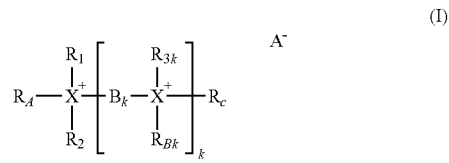

wherein (A) is an anion, and said anion is a conjugated base of a strong or weak inorganic or organic acid, or combinations thereof, and wherein the cationic compound (I) and anion (A), together, have a neutral charge,
and wherein
X is nitrogen (N),
k is the integer 1, 2, 3, or 4,
B represents a substituted or non-substituted aliphatic alkanediyl bridge, wherein the substituted aliphatic alkanediyl bridge is substituted on one or more carbon atoms, wherein one or more non-adjacent carbon atoms is replaced by oxygen, and wherein the substituted aliphatic alkanediyl bridge is the structure $(CH_2)_n$—$(OCH_2)_m$— wherein n and m independently represent the integer 0, 1, 2, 3, 4, 5, or 6, with n+m>0;
$R_1$, $R_2$ and $R_{3k}$, are independently selected from the group consisting of methyl, ethyl, propyl, isopropyl, butyl, isobutyl, n-pentyl, isopentyl, and hexyl $R_A$, $R_{Bk}$, $R_C$, are independently selected from the group consisting of an unsubstituted linear or branched $C_1$-$C_{21}$ alkyl, an unsubstituted linear or branched $C_1$-$C_{21}$ alkenyl, an unsubstituted linear or branched $C_1$-$C_{21}$ alkynyl, and a structure

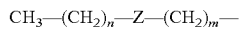

wherein n, m are independent of each other, and n represents the integer 2, 3 or 4, m represents the integer 8, 9, 10, 11, 12, 13, 14, 15, 16, 17, or 18, and Z represents —O—, —CO—, —OCO—, —CO—N—, or —N—CO—;

wherein the unpurified nucleic acid in the biological sample forms a complex with the cationic compound (1) and is stabilized from degradation within said biological sample;

dissolving the complex between the cationic compound and the unpurified nucleic acid in the biological sample to liberate the nucleic acids under non-binding or binding conditions; and optionally, isolating the stabilized nucleic acid from the biological sample.

5. The method according to any one of claims 1, 2, or 4, wherein said at least one cationic compound is added to the biological sample in the form of a solid.

6. The method according to any one of claims 1, 2, or 4, wherein said at least one cationic compound is added to the biological sample in the form of a solution, said solution being added in an amount selected from the group consisting of at least 0.001 volume, at least 0.01 volume, 0.05 volume, and 1 volume of the biological sample.

7. The method according to claim 6, wherein the solution of said at least one cationic compound has a concentration in the range of 0.01% to saturation.

8. The method according to claim 6, wherein the solution of said at least one cationic compound has a concentration in the range of 0.5 to 5%.

9. The method according to claim 6, wherein the solution of said at least one cationic compound has a concentration in the range of 2 to 4%.

10. The method according to any one of claims 1, 2, or 4, said method additionally including the following step:
mixing said at least one cationic compound with the biological sample.

11. The method according to claim 10, wherein said mixing is followed by incubating at room temperature, in order to isolate nucleic acids.

12. The method according to any one of claims 1, 2, or 4, wherein said at least one cationic compound and/or the complex formed of nucleic acid and cationic compound(s) is combined with an additional means selected from the group consisting of: means to support lysis, means for homogenization, means for mechanical exposure, means for enzymatic exposure, and combinations thereof.

13. The method according to claim 12, wherein said additional means is a means to support lysis.

14. The method according to claim 13, wherein said means to support lysis is selected from the group consisting of: an alcohol, an aldehyde, a phenol, a detergent, a sulfhydryl reducing reagent, a phosphoric acid derivative, a chaotropic reagent, a carboxylic acid, a plain salt, and combinations thereof.

15. The method according to claim 14, wherein the means to support lysis is an alcohol.

16. The method according to claim 15, wherein said alcohol is a branched or unbranched C1-C4 alkanol.

17. The method according to claim 14, wherein the means to support lysis is an aldehyde.

18. The method according to claim 17, wherein said aldehyde is a branched or unbranched C1-C4 aldehyde.

19. The method according to claim 14, wherein the means to support lysis is a detergent.

20. The method according to claim 19, wherein said detergent is ionic, zwitterionic, or non-ionic.

21. The method according to any one of claims 1, 2, or 4, wherein any complexes formed of nucleic acid and said cationic compound(s) are sedimented by centrifugation.

22. The method according to claim 21, wherein centrifugation is conducted at low g values ranging from 500 to 5000×g for 3-10 minutes.

23. The method according to claim 21, further comprising dissolving said sedimented complexes in a buffer.

24. The method according to any one of claims 1, 2, or 4, wherein the complexes of nucleic acid and said cationic compound(s) are concentrated on the surface of a membrane using vacuum, excess pressure, centrifugation, or capillary forces.

25. The method according to claim 24, wherein the complexes concentrated on the surface of a membrane are dissolved to liberate the nucleic acids, and the liberated nucleic acids are re-bound on a membrane.

26. The method according to any one of claims 1, 2, or 4, wherein the biological sample is selected from the group consisting of a food sample containing free or bound nucleic acids or nucleic acid-containing cells; an environmental sample containing free or bound nucleic acids or nucleic acid-containing cells; a cell-free sample material; a suspensions of viruses; a clinical sample; and a plant sample.

27. The method according to claim 26, wherein said biological sample is a clinical sample.

28. The method according to claim 27, wherein said clinical sample is selected from the group consisting of blood, plasma, serum, leukocyte fractions, *Crusta phlogistica*, sputum, urine, sperm, feces, and smears.

29. The method according to any one of claims 1, 2, or 4, wherein following the step of contacting the biological sample with the cationic compound(s), the method further comprises:
adding means to support lysis and/or enzymatic exposure and/or mechanical exposure of the combined sample/cationic compound(s),
mixing the sample thus obtained,
collecting resultant complexes of nucleic acid and cationic compound on the bottom of a vessel or on a membrane using centrifugation, vacuum, excess pressure and/or capillary forces,
optionally washing the complexes with a wash solution using centrifugation, excess pressure, vacuum and/or capillary forces,
optionally adding a reagent solution comprising an enzyme,
dissolving the complexes to liberate the nucleic acids under non-binding or binding conditions, and
isolating the liberated nucleic acid.

30. The method according to any one of claims 1, 2, or 4, wherein at least one of the steps is carried out automatically.

31. The method according to any one of claims 1, 2, or 4, wherein said biological sample is added to an apparatus, which apparatus carries out the steps of the method automatically.

32. The method according to claim 26, wherein said clinical sample is suspension of cells or a tissue sample.

33. The method according to claim 26, wherein said biological sample is a suspension of cells.

34. The method according to claim 33, wherein said suspension of cells is a suspension of bacteria or yeast.

* * * * *